US00RE50393E

(19) United States
(12) Reissued Patent
Dos Santos et al.

(10) Patent Number: US RE50,393 E
(45) Date of Reissued Patent: Apr. 22, 2025

(54) EXPRESSION CARTRIDGE FOR THE TRANSFORMATION OF EUKARYOTIC CELLS, METHOD FOR TRANSFORMING EUKARYOTIC CELLS, GENETICALLY MODIFIED ORGANISM, METHOD FOR PRODUCING BIOFUELS AND/OR BIOCHEMICALS, AND THUS PRODUCED BIOFUEL

(71) Applicant: BIOCELERE AGROINDUSTRIAL LTDA., Minnetrista, MN (US)

(72) Inventors: Leandro Vieira Dos Santos, São Paulo (BR); Gonçalo Amarante Guimarães Pereira, São Paulo (BR)

(73) Assignee: BIOFLEX AGROINDUSTRIAL S.A., Sao Paulo (BR)

(21) Appl. No.: 17/122,839

(22) Filed: Dec. 15, 2020

Related U.S. Patent Documents

Reissue of:
(64) Patent No.: 10,155,953
Issued: Dec. 18, 2018
Appl. No.: 15/315,081
PCT Filed: Jun. 12, 2015
PCT No.: PCT/BR2015/050075
§ 371 (c)(1),
(2) Date: Nov. 30, 2016
PCT Pub. No.: WO2015/188244
PCT Pub. Date: Dec. 17, 2015

(30) Foreign Application Priority Data

Jun. 12, 2014 (BR) ..... 102014014407

(51) Int. Cl.
*C12N 15/81* (2006.01)
*C12N 9/92* (2006.01)
*C12N 15/52* (2006.01)
*C12P 7/06* (2006.01)

(52) U.S. Cl.
CPC ..... *C12N 15/81* (2013.01); *C12N 9/92* (2013.01); *C12N 15/52* (2013.01); *C12P 7/06* (2013.01); *C12Y 503/01005* (2013.01); *Y02E 50/10* (2013.01)

(58) Field of Classification Search
CPC ..... C12N 15/81; C12N 9/92; C12N 15/52; C12P 7/06; C12Y 503/01005; Y02E 50/10
See application file for complete search history.

(56) References Cited

U.S. PATENT DOCUMENTS 6,410,302 B1 6/2002 Traff
8,399,215 B2 3/2013 Klaassen

FOREIGN PATENT DOCUMENTS

EP 2679686 A1 1/2014
WO 2006009434 A1 1/2006
WO 2011153516 A2 12/2011
WO 2014018552 A1 1/2014

OTHER PUBLICATIONS

Traff et al. (Applied and Environmental Microbiology, vol. 67, No. 12, pp. 5668-5674, Dec. 2001). (Year: 2001).*
A. Madhavan et al. "Xylose isomerase from polycentric fungus *Orpinomyces*: gene sequencing, cloning, and expression in *Saccharomyces cerevisiae* for bioconversion of xylose to ethanol", Appl. Microbiol. Biotechnol. 82:1067-1078 (2009).*

* cited by examiner

*Primary Examiner* — Lora E Barnhart Driscoll
(74) *Attorney, Agent, or Firm* — O'Connor & Company; Ryan P. O'Connor

(57) ABSTRACT

The present invention describes the expression cassette for transforming eukaryotic cell which comprises the peptide encoding non-natural sequence of nucleotides with xylose isomerase feature (SEQ ID NO: 1), optionally also comprising other genes of pentose phosphate route. Additionally, it is described the microorganism filed under the number DSM28739, which, in addition to the above-mentioned modifications, also present genetic modifications from adaptive evolution. The described microorganism shows efficient consumption of xylose and conversion of ethanol when compared to its correspondent without said genetic modifications and mutations from evolution. It is also described the process for producing biofuels e biochemicals, preferably ethanol, mainly from the lignocellulosic portion of the vegetal biomass. Biofuels, preferably ethanol, and biochemicals produced by the process of the invention are also described.

10 Claims, 5 Drawing Sheets

Specification includes a Sequence Listing.

TCGAGGAGAACTTCTAGTATATCCACATACCTAATATTATTGCCTTATTAAAAATGGAATCCCA
ACAATTACATCAAAATCCACATTCTCTTCAAAATCAATTGTCCTGTACTTCCTTGTTCATGTGT
GTTCAAAAACGTTATATTTATAGGATAATTATACTCTATTTCTCAACAAGTAATTGGTTGTTTG
GCCGAGCGGTCTAAGGCGCCTGATTCAAGAAATATCTTGACCGCAGTTAACTGTGGGAATACTC
AGGTATCGTAAGATGCAAGAGTTCGAATCTCTTAGCAACCATTATTTTTTTCCTCAACATAACG
AGAACACACAGGGGCGCTATCGCACAGAATCAAATTCGATGACTGGAAATTTTTTGTTAATTTC
AGAGGTCGCCTGACGCATATACCTTTTTCAACTGAAAAATTGGGAGAAAAAGGAAAGGTGAGAG
GCCGGAACCGGCTTTTCATATAGAATAGAGAAGCGTTCATGACTAAATGCTTGCATCACAATAC
TTGAAGTTGACAATATTATTTAAGGACCTATTGTTTTTTCCAATAGGTGGTTAGCAATCGTCTT
ACTTTCTAACTTTTCTTACCTTTTACATTTCAGCAATATATATATATATTTCAAGGATATACCA
TTCTAATGTCTGCCCCTAAGAAGATCGTCGTTTTGCCAGGTGACCACGTTGGTCAAGAAATCAC
AGCCGAAGCCATTAAGGTTCTTAAAGCTATTTCTGATGTTCGTTCCAATGTCAAGTTCGATTTC
GAAAATCATTTAATTGGTGGTGCTGCTATCGATGCTACAGGTGTCCCACTTCCAGATGAGGCGC
TGGAAGCCTCCAAGAAGGTTGATGCCGTTTTGTTAGGTGCTGTGGGTGGTCCTAAATGGGGTAC
CGGTAGTGTTAGACCTGAACAAGGTTTACTAAAAATCCGTAAAGAACTTCAATTGTACGCCAAC
TTAAGACCATGTAACTTTGCATCCGACTCTCTTTTAGACTTATCTCCAATCAAGCCACAATTTG
CTAAAGGTACTGACTTCGTTGTTGTCAGAGAATTAGTGGGAGGTATTTACTTTGGTAAGAGAAA
GGAAGACGATGGTGATGGTGTCGCTTGGGATAGTGAACAATACACCGTTCCAGAAGTGCAAAGA
ATCACAAGAATGGCCGCTTTCATGGCCCTACAACATGAGCCACCATTGCCTATTTGGTCCTTGG
ATAAAGCTAATGTTTTGGCCTCTTCAAGATTATGGAGAAAAACTGTGGAGGAAACCATCAAGAA
CGAATTCCCTACATTGAAGGTTCAACATCAATTGATTGATTCTGCCGCCATGATCCTAGTTAAG
AACCCAACCCACCTAAATGGTATTATAATCACCAGCAACATGTTTGGTGATATCATCTCCGATG
AAGCCTCCGTTATCCCAGGTTCCTTGGGTTTGTTGCCATCTGCGTCCTTGGCCTCTTTGCCAGA
CAAGAACACCGCATTTGGTTTGTACGAACCATGCCACGGTTCTGCTCCAGATTTGCCAAAGAAT
AAGGTTGACCCTATCGCCACTATCTTGTCTGCTGCAATGATGTTGAAATTGTCATTGAACTTGC
CTGAAGAAGGTAAGGCCATTGAAGATGCAGTTAAAAAGGTTTTGGATGCAGGTATCAGAACTGG
TGATTTAGGTGGTTCCAACAGTACCACCGAAGTCGGTGATGCTGTCGCCGAAGAAGTTAAGAAA
ATCCTTGCTTAAAAAGATTCTCTTTTTTTATGATATTTGTACATAAACTTTATAAATGAAATTC
ATAATAGAAACGACACGAAATTACAAAATGGAATATGTTCATAGGGTAGACGAAACTATATACG
CAATCTACATACATTTATCAAGAAGGAGAAAAAGGAGGATAGTAAAGGAATACAGGTAAGCAAA
TTGATACTAATGGCTCAACGTGATAAGGAAAAAGAATTGCACTTTAACATTAATATTGACAAGG
AGGAGGGCACCACACAAAAAGTTAGGTGTAACAGAAAATCATGAAACTACGATTCCTAATTTGA
TATTGGAGGATTTTCTCTAAAAAAAAAAAAAATACAACAAATAAAAAACACTCAATGACCTGACC
ATTTGATGGAGTTTAAGTCAATACCTTCTTGAACCATTTCCCATAATGGTGAAAGTTCCCTCAA
GAATTTTACTCTGTCAGAAACGGCCTTACGACGTAGTCGA

Figure 5

EXPRESSION CARTRIDGE FOR THE TRANSFORMATION OF EUKARYOTIC CELLS, METHOD FOR TRANSFORMING EUKARYOTIC CELLS, GENETICALLY MODIFIED ORGANISM, METHOD FOR PRODUCING BIOFUELS AND/OR BIOCHEMICALS, AND THUS PRODUCED BIOFUEL

Matter enclosed in heavy brackets [ ] appears in the original patent but forms no part of this reissue specification; matter printed in italics indicates the additions made by reissue; a claim printed with strikethrough indicates that the claim was canceled, disclaimed, or held invalid by a prior post-patent action or proceeding.

FIELD OF THE INVENTION

The present invention refers to biofuels, biochemicals and to processes for obtaining them. More specifically, the present invention provides technical solutions for producing second-generation fuels based on conversion of vegetal biomass, preferably from polymers of the vegetal cellular wall. Among other objects, the present technology describes an expression cassette for transforming eukaryotic cells and genetically modified microorganism, with efficient fermentative performance in the conversion of sugars present in vegetal biomass into biochemicals and/or biofuels. The microorganism of the present invention passed by the process of improvement by evolutionary engineering in order to increase its consumption of xylose, thus favoring its performance in industrial scale. A process for obtaining biofuels and/or biochemicals and the products thus obtained are also described.

BACKGROUND OF THE INVENTION

The need for replacement of world matrix of fuels based on fossil sources by renewable alternatives made the production of second-generation fuels, for example, ethanol, one of the most promising technologies in development phase. This process consists of conversion of polymers which form the vegetal biomass, mainly those present in cellular wall as cellulose, hemicellulose and lignin, into biofuels and/or biochemicals.

The vegetal biomass is a complex mixture of chemically distinct compounds which can be fractionated generating components with specific applications. Thus, in the same way a petrochemical refinery produces a great variety of products derived from crude oil, the same principles can be applied to biorefineries, that is, refineries based on biomass (Santos, L. V.; Pereira, G. A. G. Petroquimica verde—Anais do Simpésio Microrganismos em Agroenergia: da Prospecç ão aos Bioprocessos. Editora Embrapa. ISSN 2177-4439, 2013).

Although the use of vegetal biomass as a source of fermentable sugars is a promising and sustainable alternative, some challenges need to be overcome, like the availability of sugar from vegetal cellular wall. This procedure may be done through the action of hydrolytic enzymes (cellulases and hemicellulases), which provide the monomers of sugars (hexoses and pentoses) which are posteriorly metabolized by microorganisms for generating biochemicals and biofuels.

However, microorganisms naturally able to consume sugars present in the cellulose and hemicellulose chains, generally, are not efficiently usable in industrial scale. Thus, it is necessary to develop microorganisms with ability to use efficiently these sugars of vegetal cellular wall in industrial scale, as described in the present invention.

The use of microorganisms as efficient platforms in the conversion of biomass sugar into high added value products is widely described. In this sense, the yeast Saccharomyces cerevisiae has received prominent role due to its robustness and tolerance in industrial fermentation conditions. The ease of genetic manipulation of this organism and the use of metabolic engineering tools, in synergy with biology of systems and synthetic biology, has allowed the inclusion of new metabolic routes for producing fuels and chemicals such as ethanol, biobutanol, biodiesel, 1,2-propanediol, succinic acid, pyruvic acid, among others [Cellular and Molecular Life Sciences, 69(16):2671-90, 2012].

Wild lines of S. cerevisae are not naturally able to ferment pentoses, such as, for example, xylose, present in biomass. However, several studies have already done procedures of metabolic engineering in S. cerevisiae through the introduction in these organisms of metabolic routes for consumption of xylose, focusing on two main routes: the Xylose Reductase route—Xylitol Dehydrogenase (XR-XDH) and Xylose Isomerase (XI) route.

Among the studies carried out, the introduction of gene which encodes the xylose isomerase (XI) enzyme allows the strain to present higher yield in the production of alcohol and/or acids than when it is modified with other gene, as for example, gene encoding xylose reductase or xylitol dehydrogenase, since there is less accumulation of undesirable byproducts, such as xylitol and glycerol [2004, FEMS Yeast Res. 4: 655-664].

The XR-XDH route, present in microorganisms eukaryotes, consists of two redox reactions, where xylose is reduced to xylitol by the action of xylose reductase (XR) enzyme, in a reaction mediated by NADPH/NADH and then, xylitol is oxidized to xylulose through the xylitol dehydrogenase (XDH) enzyme, exclusively mediated by $NAD^+$. The NADPH co-factor is mainly regenerated in the oxidative phase of the pentose phosphate route, producing $CO_2$. In addition, $NAD^+$ is regenerated mainly in the respiratory chain, with the $O_2$ as final acceptor of electrons. Under limited oxygen concentrations, the complete reoxidation of $NAD^+$ does not occur, resulting in a redox unbalance and the accumulation of xylitol, which directly impacts the final yield of ethanol [Biochemical Engineering Journal, Amsterdam, v. 12, n. 1, p. 49-59, 2002]. In addition to xylitol, other byproduct formed is glycerol, due to reoxidation of excess NADH through XDH [FEMS Yeast Research, Delft, v. 4, n. 6, p. 655-664, 2004].

The xylose isomerase (XI) route, more common in prokaryotes, occurs in a single step, avoiding redox unbalance and the formation of byproducts that decrease the yield of ethanol. For several decades, attempts at heterologous expression of bacterial XI in S. cerevisiae were not successful [Enzyme and Microbial Technology, Amsterdam, v. 32, n. 2, p. 252-259, 2003]. In 2003, the functional expression in S. cerevisiae of a xylose isomerase of anaerobic fungus Piromyces sp. [FEMS Yeast Research, Delft, v. 4, n. 1, p. 69-78, 2003] and in 2009 of Orpiromyces sp. fungus [Applied Microbiology and Biotechnology, Heidelberg, v. 82, n. 6, p. 1067-1078, 2009], resulted in mutants able to grow in xylose as the only source of carbon, with high activities of these enzymes, higher yield in the production of ethanol, lower production and accumulation of intermediate metabolites and with less catabolic repression in medium containing glucose and xylose [FEMS Yeast Research, Delft, v. 4, n. 6, p. 655-664, 2004; FEMS Yeast Research, Delft, v. 5, n. 4, p. 399-409, 2005a; FEMS Yeast Research, Delft, v. 5, n. 10, p. 925-934, 2005b]. The XR-XDH route has higher initial productivity for producing ethanol more rapidly, only with the insertion of the genes responsible for conversion of xylose, however, the XI route has a higher yield for not accumulating byproducts [Microbial Cell Factories, Londres, v. 6, n. 5, p. 1-10, 2007].

Many documents, as, for example, W02006/009434, WO2011/153516, U.S. Pat. No. 8,399,215, EP2679686 and WO2014018552 describe microorganisms able to use pentoses, more specifically xylose, as a source of carbon. In order to be able to consume xylose, it is necessary that the microorganism is genetically modified at least with the addition of the gene encoding xylose isomerase. As a strategy to improve yeast productivity, the genes encoding Xylulokinase and the genes of the pentoses phosphate route can be overexpressed: Transketolase, ribose 5-phosphate isomerase, ribose 5-phosphate epimerase and Transaldolase. Furthermore, the inactivation of the gene encoding an aldose reductase (GRE3) can be performed, aiming for a lower accumulation of xylitol and a higher yield of ethanol.

Therefore, the literature shows that increased expression of the genes described above that favor the conversion of xylose to ethanol is necessary for the consumption of this sugar is efficient. Thus, the microorganisms described in the prior art, which were genetically modified for consumption of xylose, can have (but not necessarily) the genetic modifications described above. What basically differentiates the efficiency and productivity in the anaerobic conversion of xylose in biofuels and/or biochemicals presented by each one of these is the form and location how these genes are incorporated to the microorganism genome, considering the best possible combination between these genes and respective promoters by which they are regulated, as well as the appropriate choice by the sequence of nucleotides encoding xylose isomerase, being this the main gene that, when expressed, enables the consumption of xylose for each modified microorganism, in addition to adaptation of microorganism through evolution. Thus, the present invention shows advantageously better yield and productivity than the microorganisms previously described in the prior art.

The present invention describes, among other objects, a genetically modified microorganism for inclusion of genes of the pentose phosphate route, as well as those of Xylulokinase, and inactivation of the aldose reductase gene, as described in the documents WO2006/009434, WO2011/153516, U.S. Pat. No. 8,399,215, EP2679686 and WO2014018552. The genetically modified microorganism of the present invention differs advantageously from the previous one by the fact that the genes have been more efficiently combined with their promoters, as well as inserted into more convenient location in the microorganism genome, when compared to the previously mentioned documents. Additionally, the gene encoding xylose isomerase herein inserted has been optimized, by the inventors, for the preferably codons of microorganism in which it was first inserted, in this case, the microorganism of Saccharomyces cerevisiae species. In the present document, the genes are inserted into the microorganism through the homologous recombination, then going to interact with its genome.

Specifically, referring to the production of ethanol, the obtaining of some lines able to act in industrial scale was successful. However, such strains are still susceptible to have their fermentative performance compromised or even be replaced by wild lines when subjected to the stressful conditions of the Brazilian process of ethanol production.

In the Brazilian fermentative process for ethanol production, it is usual that the plants do the intensive reuse of yeast cells used in the fermentation, process known as recycling. In this process, up to 90% of yeasts may be reused from one fermentation to another, resulting in very high cell densities inside the fermenter and making the fermentation time very short [FEMS yeast research, 8(7):1155-63, 2008].

In some industrial pants, the recycling can occur throughout the period harvest, lasting up to nine months. Thus, the prolonged period of recycling added to continuous input of microbial contaminants into the system, makes the fermentation environment highly competitive, imposing severe biotic and abiotic tensions on the strains of yeast used in the process [International Sugar Journal, Londres, v. 112, p. 86-89, 2010]. This competitive environment results in the replacement of yeasts which started the fermentation process by wild yeasts. This fact happens because the wild yeasts naturally occur in sugarcane and, therefore, are inserted together with it in the process of fermentation, thus ending up contaminating the entire industrial process [FEMS yeast research, 8(7):1155-63, 2008].

Additionally, some studies demonstrated that those yeasts that started the fermentation process, and ended up being replaced by the wild, are also not able to survive stressful situations of the industrial process of fermentation, such as high concentration of ethanol, high temperature, osmotic stress due to salts and sugars, acidity, sulfites and bacterial contamination [FEMS yeast research, 8(7):1155-63, 2008]. Thus, the obtaining of line with efficient capacity of resistance to the aggressive industrial process of fermentation, as well as susceptible to genetic modifications to acquire characteristics of interest, such as the consumption of pentoses, more specifically xylose, is not a trivial process.

The microorganism described in the present invention, therefore, is advantageously adapted to the Brazilian process of industrial fermentation and is shown to be differentially efficient in the conversion of sugars from vegetal biomass, mainly lignocellulosic material, to biofuels and/or biochemicals, that is, with sufficient yield to be applied in industrial scale, even under the stressful conditions of the Brazilian fermentation process.

Additionally, the microorganism described in the present invention shows features of industrial interest such as: being a non-flocculating strain, presenting high yield of ethanol, low formation of glycerol and xylitol, high viability, high growth rate, non-production of foam, among others.

BRIEF DESCRIPTION OF THE INVENTION

It is one of the objects of the present invention an expression cassette for transforming eukaryotic cell characterized in that it comprises:

a) at least one nucleotide sequence selected from the group consisting of: xylose isomerase (SEQ ID NO: 1), transaldolase (SEQ ID NO: 5), ribose 5-phosphate isomerase (SEQ ID NO: 7), xylulokinase (SEQ ID NO: 9), transcetolase (SEQ ID NO: 11) and ribose 5-phosphate epimerase (SEQ ID NO: 12);

b) at least one promoter nucleotide sequence selected from the group consisting of: promoter glyceraldehyde 3-phosphate dehydrogenase (SEQ ID NO: 2), promoter 3-phosphate kinase (SEQ ID NO: 6), promoter of alcohol dehydrogenase enzyme 1 (SEQ ID NO: 8);

c) at least one terminator nucleotide sequence selected from the group consisting of: terminator glyceraldehyde 3-phosphate dehydrogenase (SEQ ID NO: 3), terminator alcohol dehydrogenase (SEQ ID NO: 10), terminator 3-phosphate kinase (SEQ ID NO: 13);

and wherein the nucleotide sequence defined in a) is functionally linked to the promoter nucleotide sequence defined in b) and to the terminator nucleotide sequence defined in c), being heterologous any one of said sequences.

It is another object of the present invention a process for transforming eukaryotic cell comprising the introduction, in the cell to be transformed, of at least an expression cassette as defined by the present invention.

It is another object of the present invention a genetically modified microorganism comprising at least an expression cassette as defined by the present invention.

It is another object of the present invention the genetically modified microorganism Saccharomyces cerevisiae DSM28739.

It is another object of the present invention a process for producing biofuels and/or biochemicals which comprise the step of cultivation of microorganism as defined by the present invention.

It is another object of the present invention the biofuel that is obtained by the process as defined by the present invention.

It is another object of the present invention the biochemical which is obtained by the process as defined by the present invention.

The present invention describes a genetically modified microorganism with efficient fermentative performance in the conversion of sugars contained in vegetal biomass, in biofuels and/or biochemicals, when compared to its version without the genetic modifications described in the present document. More specifically, the genetically modified microorganism described in the present invention refers to any eukaryotic cell susceptible of genetic transformation, which can consist of yeasts or filamentous fungi, preferably yeast of Saccharomyces genus.

The microorganism of the invention provides efficient performance in the conversion of sugars present in the vegetal biomass, preferably lignocellulosic material, in biochemicals and/or biofuels. Thusr, in one embodiment, the present invention describes a microorganism of the Saccharomyces cerevisiae species more efficient that its correspondent without the genetic modifications in the conversion of pentoses present in the lignocellulosic material in alcohols and/or biochemicals, such as, for example, succinic acid, malic acid, 1,3-propanediol, 1,2-propanediol, butanol, isobutanol, biodiesel, 1,4-butanediol, 2,3-butanediol, PHB—poly(butyrate hydroxide), however, without being restricted to these, without however being restrict to it.

The microorganism described in the present invention is genetically modified by the introduction of sequence of nucleotides encoding a peptide with xylose isomerase function. This sequence was originally described in Orpinomyces sp. [Appl Microbiol Biotechnol, 82:1067-1078, 2009] (XI, EC 5.3.1.5) and manually optimized by the present inventors for the codons preferably used for Saccharomyces cerevisiae. The optimization comprises comparison between codons present in the sequence of Orpinomyces with those preferably used for Saccharomyces aiming to replace the same keeping, however, the proportion of codons present in Saccharomyces. The optimized sequence of xylose isomerase described in the present invention (represented in SEQ ID NO: 1) is, however, not natural and different from natural sequences of xylose isomerase already described. SEQ ID NO: 1 can also be useful for insertion in eukaryotic cell and expressed in its active form. The sequence of nucleotides SEQ ID NO: 1 can present in single copy or multiple copies in the genome.

The genetically modified host eukaryotic cell (target cell) may, additionally, contain genes of the pentose phosphate route, aiming increased speed of xylose conversion. However, Additionally to the insertion of SEQ ID NO: 1 in host cell, the present invention describes genetic modifications in the same cell aiming the favoring of metabolic flow through the pentose phosphate route, these modifications, however, not being a restrictive factor for transforming the host cell with the sequence of nucleotides represented in SEQ ID NO: 1.

In order to increase the flow of the phosphate pentoses route in the host cell, new copies of the genes encoding Xylulokinase enzymes are inserted (XKS1, EC 2.7.1.17), whose sequence of nucleotides is represented in this document by SEQ ID NO: 9, Transaldolase (TAL1, EC 2.2.1.2), represented by SEQ NO ID:5, Transcetolase (TKL1, EC 2.2.1.1), represented by SEQ ID NO: 11, Ribose 5-Phosphate Isomerase (RKI1, EC 5.3.1.6), represented by SEQ ID NO: 7; and Ribose 5-Phosphate Epimerase (RPE1, EC 5.1.3.1), represented by SEQ ID NO: 12.

Among the enzymes presented and which constitute the pentose-phospate route, at least one of the genes encoding them must be overexpressed and, preferably, linked to constitutive promoters, that is, those that are constantly expressed, regardless of the condition to which the cell is subjected, or naturally inducible promoters. In the present document, promoters are defined as a regulatory region, located in the 5' region of the gene under its action and responsible for the beginning of transcription, while terminators are defined as a sequence which determines the end of the gene during the transcription process.

The present invention further describes expression cassettes containing one or more endogenous enzymes genes from the non-oxidative phase of the pentoses phosphate route, for transforming eukaryotic cells. Such expression cassettes or gene constructs preferably comprise strong and constitutive promoters of the cell into which they will be inserted. Specifically, four embodiments of integrative expression cassettes constructed using strong and constitutive promoters of Saccharomyces cerevisiae and stably integrated into the host cell genome are described in the present specification.

One of the cassettes disclosed contains the gene encoding xylose isomerase, SEQ ID NO: 1 and is inserted into the host cell functionally linked and/or flanked, preferably, by the promoter and terminator region of the gene Glyceraldehyde 3-Phosphate Dehydrogenase, isoenzyme 1 (TDH1). A second cassette disclosed contains the gene encoding the enzyme Xylulokinase (SEQ ID NO: 9) is preferably constructed using the promoter and terminator of the gene encoding alcohol dehydrogenase enzyme (ADH1). A third cassette described in the present invention contains encoding genes of Transaldolase (SEQ NO ID:5) and Ribose 5-Phosphate Isomerase (SEQ ID NO: 7) and is constructed, preferably using promoters and terminators of the gene encoding the Glyceraldehyde 3-Phosphate Dehydrogenase enzyme, isoenzyme 1 (TDH1) to flank the gene of Transaldolase and promoters and terminators of 3-phosphoglycerate Kinase enzyme (PGK1) to flank the gene of Ribose 5-Phosphate Isomerase. The last cassette described in the present invention contains encoding genes of Transcetolase (SEQ ID NO: 11) and Ribose 5-Phosphate Epimerase (SEQ ID NO: 7). It is constructed, preferably, under the action of promoters and terminators of Glyceraldehyde 3-Phosphate Dehydrogenase genes, isoenzyme 1 (TDH1), flanking the gene of Transcetolase and promoter and terminator of gene encoding the 3-phosphoglycerate Kinase enzyme (PGK1).

Said expression cassettes with the genes of metabolic route of pentose phosphate favoring the consumption of xylose are introduced in the eukaryotic cell and respective genes are inserted in the target chromosome located between the centromere and the first gene adjacent to it, preferably in the region of 5 thousand first base pairs counted from the centromere both in the upstream and downstream direction, which may be even just upstream, just downstream or both simultaneously.

Additionally to the insertion of expression cassettes, the present invention describes the gene deletion GRE3 of host eukaryotic cell, which encodes an aldose reductase and is represented in SEQ ID NO: 14.

Furthermore, the present invention describes the stable integration and in high number of copies of cassette expressing XI (SEQ ID N:1) in the host cell genome. In the present document, it is considered high number of copies the insertion of, at least, 5 copies of the gene in question, the insertion of at least 20 copies being preferential.

The present document describes, therefore, a eukaryotic cell, preferably microorganism of Saccharomyces cerevisiae species, genetically modified containing in its genome at least one of genes of the enzymes needed to favor the non-oxidative part of the pentose phosphate routes, inserted preferably in high number of copies and in the region between the centromere and its first adjacent gene.

Additionally, a microorganism is described, which in addition to the above-represented genetic manipulation, was subjected to procedure of evolutionary engineering in order to generate random mutations which favor greater consumption of lignocellulosic portion of the vegetal biomass, preferably xylose in anaerobic medium and, accordingly, higher growth rate and higher production of biochemical compounds and/or biofuels, preferably ethanol, by time frame, when compared with the microorganism before the evolution process. The genetically modified microorganism described in the present invention presents differently the features of being non-flocculating, presenting high ethanol, yield, low glycerol and xylitol formation, high viability, high growth rate, non-production of foam, in addition to efficient ability of resistance to the aggressive fermentation process. This evolved microorganism was filed by the inventors in the German Collection of Microorganisms and Cell Culture-Leibniz-Institut DSMZ, having received the number DSM28739.

The microorganism DSM28739 described in the present invention shows features of industrial interest such as: being a non-flocculating strain, presenting high ethanol yield, low glycerol and xylitol formation, high viability, high growth rate, non-production of foam, among others.

Furthermore, the present invention describes the process of producing biofuels and biochemicals from vegetal biomass. More specifically, the process for producing biofuels and biochemicals preferably uses the lignocellulosic portion of the vegetal biomass. The process described in the present invention uses the microorganism of the invention, preferably DSM28739, for producing biofuels and/or biochemicals.

BRIEF DESCRIPTION OF THE DRAWINGS

In FIG. 5, it is shown the sequence of nucleotides represented as SEQ ID NO: 17, being indicated the region encoding LEU2 (underlined), along with its promoter and terminator (not underlined).

DETAILED DESCRIPTION OF THE INVENTION

Figure 1:
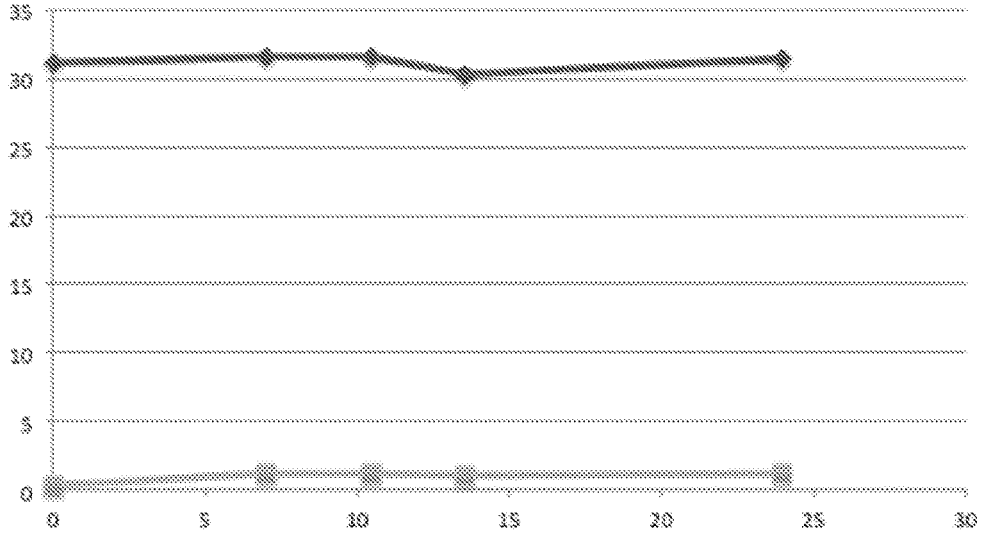
In FIG. 1, it is noted the consumption of xylose and ethanol production under anaerobic conditions by the microorganism described in the present invention after the process of genetic manipulation for insertion of genes of the pentose phosphate route and genetically modified gene of xylose isomerase, SEQ ID NO: 1, and before the evolution process. In the vertical axis, the concentration is described in grams per liter (g/L) and in the horizontal axis, the time in hours. The concentration of xylose is indicated by (♦), while the concentration of ethanol by time, is represented by (■).

It is one of the objects of the present invention an expression cassette for transforming eukaryotic cell comprising:

a) at least one nucleotide sequence selected from the group consisting of: xylose isomerase (SEQ ID NO: 1), transaldolase (SEQ ID NO: 5), ribose 5-phosphate isomerase (SEQ ID NO: 7), xylulokinase (SEQ ID NO: 9), transcetolase (SEQ ID NO: 11) and ribose 5-phosphate epimerase (SEQ ID NO: 12);

b) at least one promoter nucleotide sequence selected from the group consisting of: promoter glyceraldehyde 3-phosphate dehydrogenase (SEQ ID NO: 2), promoter 3-phosphate kinase (SEQ ID NO: 6), promoter of alcohol dehydrogenase 1 enzyme (SEQ ID NO: 8);

c) at least one terminator nucleotide sequence selected from the group consisting of: terminator glyceraldehyde 3-phosphate dehydrogenase (SEQ ID NO: 3), terminator of alcohol dehydrogenase (SEQ ID NO: 10), terminator 3-phosphate kinase (SEQ ID NO: 13);

and wherein the nucleotide sequence defined in a) is functionally linked to the promoter nucleotide sequence defined in b) and to the terminator nucleotide sequence defined in c), being heterologous any one of said sequences.

In one embodiment, the expression cassette is selected from the group consisting of:

a) expression cassette which comprises gene encoding xylose isomerase of sequence SEQ ID NO: 1, TDH1 promoter of nucleotide sequence SEQ ID NO: 2, and TDH1 terminator of nucleotide sequence SEQ ID NO: 3;

b) expression cassette which comprises ADH1 promoter represented by the sequence SEQ ID NO: 8, XKS1 gene represented by the sequence SEQ ID NO: 9 and ADH1 terminator represented by the sequence SEQ ID NO: 10;

c) expression cassette which comprises TDH1 promoter of nucleotide sequence SEQ ID NO: 2, TAL1 gene of sequence SEQ ID NO: 5, TDH1 terminator gene of sequence SEQ ID NO: 3, followed by PGK1 promoter of sequence SEQ ID NO: 6, by RKI1 gene (SEQ ID NO: 7) and by terminator of nucleotide sequence SEQ ID NO: 13;

d) expression cassette which comprises TDH1 promoter of sequence SEQ ID NO: 02, TKL1 gene of sequence SEQ ID NO: 11, encoding gene of Ribose 5-Phosphate Epimerase (SEQ ID NO: 7), TDH1 terminator of sequence SEQ ID NO: 3, followed by PGK1 promoter of sequence SEQ ID NO: 6, RPE1 gene of sequence SEQ ID NO: 12 and PGK1 terminator of sequence SEQ ID NO: 13; and combinations of at least two expression cassettes as described above;

and wherein said expression cassette(s) is/are functional in the eukaryotic cell(s).

In one embodiment, said promoter(s) is/are constitutive or naturally inducible.

It is another object of the present invention, the process for transforming the eukaryotic cell comprising the introduction, in the cell to be transformed, of at least one expression cassette as revealed by the present invention. In one embodiment, the introduction is in the genome of the cell to be transformed.

In one embodiment, the expression cassette further comprises the inactivation or deletion of the gene GRE3 (SEQ ID NO: 14) in the genome of said eukaryotic cell.

It is another object of the present invention, a genetically modified microorganism comprising at least one expression cassette as defined in the present patent application.

In one embodiment, one or more of said expression cassettes are present in the region of 5 thousand first base pairs counted from centromere both in upstream and downstream direction, which may be even just upstream, just downstream or both simultaneously.

In one embodiment, the promoter sequences, encoding sequences and terminator sequences of expression cassettes are stable in the microorganism genome and/or are present in at least 5 copies in the microorganism genome.

In one embodiment, the GRE3 gene (SEQ ID NO: 14) is inactivated or deleted in/from its genome.

In one embodiment, the microorganism is yeast of genus selected from the group consisting of: Saccharomyces, Scheffersomyces, Spathaspora, Pichia, Candida, Kluyveromyces, Schizosaccharomyces, Brettanomyces, Hansenula and Yarrowia.

In one embodiment, the microorganism is Saccharomyces cerevisiae DSM28739.

It is another object of the present invention the genetically modified microorganism Saccharomyces cerevisiae DSM28739.

It is another object of the present invention the production process of biofuels and/or biochemicals comprising a step of microorganism cultivation as defined in the present invention.

In one embodiment, the process yield is of at least 0.45 grams of ethanol produced by gram of xylose consumed by microorganism in synthetic medium which comprises xylose as source of carbon.

In one embodiment, the volumetric productivity is of at least 0.67 grams of ethanol produced by liter each hour, when in synthetic medium which comprises xylose as source of carbon.

In one embodiment, the microorganism is the microorganism Saccharomyces cerevisiae DSM28739.

It is another object of the present invention a biofuel obtained by the production process of biofuels and/or biochemicals comprising a step of microorganism cultivation as defined in the present invention.

It is another object of the present invention a biochemical obtained by the production process of biofuels and/or biochemicals comprising a step of microorganism cultivation as defined in the present invention.

The present invention describes, among other objects, a genetically modified microorganism with efficient fermentative performance in the conversion of sugars contained in the vegetal biomass, in biofuels and/or biochemicals, when compared to its version without the genetic modifications described in the present document.

More specifically, the genetically modified microorganism described in the present invention refers to a genetically transformed eukaryotic cell, preferably yeast or filamentous fungi.

In this invention, yeasts are considered as any subject from the group Eumycotina, that is, true fungi, which grow unicellularly and which make preferably anaerobic fermentation, such as, for example, Saccharomyces, Scheffersomyces, Spathaspora, Pichia, Candida, Kluyveromyces, Schizosaccharomyces, Brettanomyces, Hansenula and Yarrowia.

Filamentous fungi, in turn, are those characterized by having vegetative mycelium and growing from the hyphal elongation, in addition to performing aerobic respiration, such as, for example, Aspergillus, Penicillium, Fusarium, Trichoderma, Moniliophthora and Acremonium.

Even more specifically, the present invention describes a genetically modified microorganism, preferably yeast of Saccharomyces genus.

The described microorganism presents efficient performance in the conversion of sugars present in the vegetal biomass, preferably lignocellulosic material, in biochemicals or biofuels. One embodiment of the invention describes a microorganism of Saccharomyces cerevisiae species more efficient in the conversion of pentoses present in the lignocellulosic material in alcohols and/or biochemicals, such as, for example, succinic acid, malic acid, 1,3-propanediol, 1,2-propanediol, butanol, isobutanol, biodiesel, 1,4-butanediol, 2,3-butanediol, PHB—poly(butyrate hydroxide), however, without being restricted to these, when compared to its version without the genetic modifications contained in the present document.

Pentose preferably used by microorganism for conversion in alcohols and/or biochemicals above indicated is xylose, without however be restricted to it.

In the present invention, references are made to several gene sequences, all listed in the Sequence Listing section. For brief reference and ease of understanding, its respective functions or genes are indicated in the following table 1.

TABLE 1

Sequences referred to in the present invention and respective genes/functions.

| Gene/function | Sequence |
|---|---|
| Xylose Isomerase | SEQ ID NO: 1 |
| Promoter Glyceraldehyde 3-Phosphate Dehydrogenase, isoenzyme 1 (TDH1) | SEQ ID NO: 2 |
| Terminator Glyceraldehyde 3-Phosphate Dehydrogenase, isoenzyme 1 (TDH1) | SEQ ID NO: 3 |
| URA3 e loxp | SEQ ID NO: 4 |
| Transaldolase (TAL1) | SEQ ID NO: 5 |
| Promoter 3-Phosphate Kinase (PGK1) | SEQ ID NO: 6 |
| Ribose 5-Phosphate Isomerase (RKI1) | SEQ ID NO: 7 |
| Promoter of Alcohol Dehydrogenase 1 enzyme (ADH1) | SEQ ID NO: 8 |
| Xylulokinase (XKS1) | SEQ ID NO: 9 |
| Terminator of Alcohol Dehydrogenase (ADH1) | SEQ ID NO: 10 |
| Transcetolase (TKL1) | SEQ ID NO: 11 |
| Ribose 5-Phosphate Epimerase (RPE1) | SEQ ID NO: 12 |
| Terminator 3-Phosphate Kinase (PGK1) | SEQ ID NO: 13 |
| Aldose Reductase (GRE3) | SEQ ID NO: 14 |
| Recombinase CRE | SEQ ID NO: 15 |
| LTR of retrotransposon Ty1 | SEQ ID NO: 16 |
| LEU2 (ORF + promoter and terminator) | SEQ ID NO: 17 |

The sequence of nucleotides represented by SEQ ID NO: 1, which encodes a peptide with xylose isomerase feature, when inserted in eukaryotic cell, provides an expression of an enzyme favoring the isomerization of xylose into xylulose.

The microorganism described in the present invention is genetically modified by the introduction of sequence of nucleotides encoding a peptide with xylose isomerase function. This of nucleotides, originally described in Orpinomyces sp. (XI, EC 5.3.1.5), was manually optimized by the inventors for the codons preferably used by Saccharomyces cerevisiae. The optimized sequence of xylose isomerase used in the present invention is, however, not natural and different from natural sequences of xylose isomerase already described in public banks and is represented in SEQ ID NO: 1.

After optimization of the sequence represented in SEQ ID NO: 1, the CAI (Codon Adaptation Index), index which determines the possibility of high levels of protein expression, was 0.79 to 0.91, indicating the obtaining of an efficient expression of this protein in S. cerevisiae. The CAI index is the geometric mean of relative values of adaptation and for its calculation, non-synonymous codons are excluded and, in some cases, also those of termination. The values vary between 0 and 1, and larger ones indicate higher proportion of the most abundant codons [Nucleic Acids Research 15: 1281-1295].

Thus, the present invention also describes an expression cassette which comprises the sequence of nucleotides represented in SEQ ID NO: 1, encoding the peptide of xylose isomerase type and that, optionally, can be inserted into eukaryotic cell for the expression of said isomerase in its active form. In the present document, the genes are inserted into microorganism through the homologous recombination, thus starting to integrate its genome. The expression cassette of the invention is characterized in that it comprises: —a sequence (SEQ ID NO: 1) of nucleotides encoding a peptide with xylose isomerase function; —at least one promoter for said encoding nucleotide sequence; and—one nucleotide sequence selected from: one terminator nucleotide sequence of transcription; one selection marker; one or more encoding nucleotide sequence(s) of other enzymes; combinations thereof or one plasmid comprising such sequences, being heterologous at least one of nucleotide sequences defined above. One or more expression cassettes may be used in the transformation of eukaryotic cells according to the invention.

Optionally, the expression cassette of the invention also comprises sequences selected from the group which comprises the encoding sequences of Xylulokinase enzymes (SEQ ID NO: 9), Transaldolase (SEQ NO ID:5), Transcetolase (SEQ ID NO: 11), Ribose 5-Phosphate Isomerase (SEQ ID NO: 7) and/or Ribose 5-Phosphate Epimerase (SEQ ID NO: 12).

In one embodiment, the eukaryotic/microorganism host cell is yeast of the Saccharomyces cerevisiae species, however, it should be noted that any eukaryotic cell may be transformed with one or more expression cassettes of the invention, which comprises the sequence of nucleotides described in SEQ ID NO: 1.

Therefore, the present invention provides a eukaryotic cell, yeasts or filamentous fungi, preferably yeast of the Saccharomyces cerevisiae species, transformed with the sequence of nucleotides described in SEQ ID NO: 1, which can be presented in a single copy or, preferably, multiple copies of this sequence of nucleotides can be inserted into the genome.

In one embodiment, the genetically modified host cell further comprises genes of the pentose phosphate route, so that the insertion of SEQ ID NO: 1, which encodes xylose isomerase, favors the isomerization of xylose in xylulose. However, additionally to the insertion of SEQ ID NO: 1 in the host cell, the present invention describes genetic modifications in the same cell aiming to favor the metabolic flow through the routes of pentose phosphate, not being such modifications, however, a restrictive factor for transforming the host cell with the sequence of nucleotides represented in SEQ ID NO: 1.

For increased flow of pentose phosphate route in the host cell, genes encoding the enzymes Xylulokinase are inserted (XKS1, EC 2.7.1.17), whose sequence of nucleotides is represented in this document by SEQ ID NO: 9, Transaldolase (TAL1, EC 2.2.1.2), represented by the sequence SEQ NO ID:5, Transcetolase (TKL1, EC 2.2.1.1), whose sequence of nucleotides is represented by SEQ ID NO: 11, Ribose 5-Phosphate Isomerase (RKI1, EC 5.3.1.6), whose sequence of nucleotides is represented by SEQ ID NO: 7; and Ribose 5-Phosphate Epimerase (RPE1, EC 5.1.3.1), whose sequence of nucleotides is represented by SEQ ID NO: 12.

Among the enzymes presented, and that constitute the pentose-phosphate route, as well as the xylose isomerase represented by SEQ ID NO: 1, at least one the genes encoding them must present itself overexpressed and, preferably, linked to the constitutive promoters, that is, those that are constantly expressed, regardless of the condition to which the cell is subjected, or naturally inducible promoters. In the present document, promoters are defined as a regulatory region, located in the 5' region of the under its action and responsible for the start of transcription, while terminators are defined as a sequence which determines the final of the gene during the transcription process.

The overexpression of the genes encoding these enzymes can be due to the increased number of copies of the sequence of nucleotides encoding them, expression of episomal genes present in vector that can be inserted in the eukaryotic host cell, through the use of heterologous promoters to that sequence in which it is operably linked, or even homologous of the cell where they were inserted, or as endogenous in the host cell, as long as they are able to produce a stable state of transcription higher than would be achieved by the cell in its version without the present genetic modifications, in the situations wherein the sources of carbon as glucose and xylose are available in the environment. These promoters may be constitutive or naturally inducible.

In one embodiment, the present invention describes host cell comprising an expression cassette containing endogenous genes of enzymes of the non-oxidative phase of the pentoses phosphate route, which are, preferably, constructed using strong and constitutive promoters of the cell in which they will be inserted. Specifically, the present invention describes four embodiments of integrative expression cassettes, which were constructed using high expression and constitutive promoters of Saccharomyces cerevisiae, and stably integrated to the host cell genome.

One of the described cassettes contains the gene encoding xylose isomerase, SEQ ID NO: 1. In this cassette, a copy of SEQ ID NO: 1 is inserted into the flanked host cell, preferably, by the promoter and terminator region of the gene Glyceraldehyde 3-Phosphate Dehydrogenase, isoenzyme 1 (TDH1). Thus, briefly, the cassette which contains the gene encoding xylose isomerase and that was inserted into the host cell genome is formed by the promoter TDH1, whose sequence of nucleotides is represented by SEQ ID NO: 2, gene XI (SEQ ID NO: 1) and terminator TDH1, whose sequence of nucleotides is represented by SEQ ID NO: 3.

A second cassette described in the present invention, contains gene encoding the enzyme Xylulokinase (SEQ ID NO: 9). The present description indicates that the cassette is, preferably, constructed using gene promoter and terminator of the gene encoding alcohol dehydrogenase enzyme (ADH1). Thus, it is described that the cassette which contains the encoding gene of Xylulokinase is constructed by the promoter ADH1, represented by SEQ ID NO: 8, XKS1 gene (SEQ ID NO: 9) and terminator ADH1, represented by SEQ ID NO: 10.

One more cassette described in the present invention contains encoding genes of Transaldolase (SEQ NO ID:5) and Ribose 5-Phosphate Isomerase (SEQ ID NO: 7). This cassette is constructed, preferably using promoters and terminators of the gene encoding enzyme Glyceraldehyde 3-Phosphate Dehydrogenase, isoenzyme 1 (TDH1) to flank the gene Transaldolase and promoters and terminators of the enzyme 3-phosphoglycerate Kinase (PGK1) to flank the gene of Ribose 5-Phosphate Isomerase. Thus, briefly, the expression cassette is constructed, preferably, of promoter TDH1 (SEQ ID NO: 2), gene TAL1 (SEQ ID NO: 5) and terminator TDH1 (SEQ ID NO: 3), followed by promoter PGK1, whose sequence of nucleotides is represented by SEQ ID NO: 6, gene RKI1 (SEQ ID NO: 7) and terminator, whose sequence of nucleotides is represented by SEQ ID NO: 13.

The last cassette described in the present invention contains encoding genes of Transcetolase (SEQ ID NO: 11) and Ribose 5-Phosphate Epimerase (SEQ ID NO: 7), preferably, with associated function to the promoters and terminators of the genes Glyceraldehyde 3-Phosphate Dehydrogenase, isoenzyme 1 (TDH1), flanking the gene of Transcetolase and promoter and terminator of the gene encoding the enzyme 3-phosphoglycerate Kinase (PGK1). Thus, briefly, the expression cassette which was inserted into the host cell genome and contains the genes of Transcetolase and Ribose 5-Phosphate Epimerase, is constructed preferably by promoter TDH1 (SEQ ID NO: 2), gene TKL1 (SEQ ID NO: 11) and terminator TDH1 (SEQ ID NO: 3), followed by promoter PGK1 (SEQ ID NO: 6), gene RPE1 (SEQ ID NO: 12) and terminator PGK1 (SEQ ID NO: 13).

All expression cassettes with the genes of metabolic route of pentose phosphate favoring the consumption of xylose are inserted into the region of the target chromosome located between the centromere and the first gene adjacent to it, preferably in the region of 5 thousand first base pairs counted from the centromere both in upstream and downstream direction, and may even be just upstream, just downstream or both simultaneously.

The upstream direction is considered that located previously to the start point of the transcription unit of a DNA sequence, which starts in the promoter and ends in the terminator. In turn, downstream is considered the region located after the start point of the transcription unit of a DNA sequence.

In addition to the insertion of expression cassettes, the present invention also describes the deletion or inactivation of the GRE3 gene, which encodes aldose reductase and is represented in SEQ ID NO: 14. The production of xylitol reduces the total yield of ethanol which can be obtained. In addition, xylitol is an inhibitor of the action of xylose isomerase enzyme.

When performed in Saccharomyces cerevisiae, the above-mentioned genetic modifications favor the flow of the non-oxidative part of the pentose-phosphate route.

Then, the Example 4, shows that the simple insertion of the gene favoring the metabolic flow by the pentose phosphate route, as well as the gene encoding peptide of xylose isomerase type in the host cell, does not guarantee efficient consumption of pentoses present in the medium.

Therefore, the present invention describes the stable integration and high number of copies of cassette expressing XI (SEQ ID N:1) in the host cell genome. In the present document, it is considered high number of copies the insertion of, at least, 5 copies of gene in question, being preferential the insertion of at least 20 copies.

The present document describes, however, and eukaryotic cell, preferably microorganism of the Saccharomyces cerevisiae species, genetically modified containing in its genome at least one of the genes of enzymes needed to favor the non-oxidative part of the pentose phosphate route, inserted preferably in high number of copies and in the region between the centromere and its first adjacent gene. By having all metabolic route needed to convert xylose, in aerobic conditions, the line is able to consume the xylose present in the cultivation medium, but in anaerobic conditions, the consumption is very slow.

In the present invention, it is further described a process of directed evolution from which is obtained a microorganism with greater capacity of xylose consumption in anaerobic conditions and, thereafter, higher growth rate and higher production of biochemicals compounds and biofuels by time frame, when compared with the microorganism that was not subjected to said process. In said process, a microorganism of the Saccharomyces cerevisiae species was subjected to evolutionary pressures which consisted of progressive increases of xylose concentration as the only source of carbon, in order to select microorganisms with random mutations which favor higher consumption of xylose in anaerobic conditions and, accordingly, higher growth rate and higher production of biochemicals compounds and biofuels, preferably ethanol. Example 4 shows comparative results between the microorganism resulting from this process and the microorganism before the process of directed evolution. The genetically modified microorganism described in the present invention presents differentially the features of being non-flocculating, presenting high yield of ethanol, low formation of glycerol and xylitol, high viability, high growth rate, non-production of foam, in addition to efficient capacity of resistance to the stressful process of industrial fermentation. This microorganism is filed in the German Collection of Microorganisms and Cell Culture-Leibniz-Institut DSMZ, under number DSM28739.

The microorganism DSM28739 described in the present invention shows features of industrial interest such as: being a non-flocculating strain, presenting high yield of ethanol, low formation of glycerol and xylitol, high viability, high growth rate, non-production of foam, among others.

Further, the present invention describes a production process of biofuels and biochemicals from vegetal biomass, preferably a lignocellulosic portion of the vegetal biomass. The process described in the present invention uses the microorganism of the invention for producing biofuels and/or biochemicals.

In one embodiment, the process consists in the following steps:

- put the microorganism DSM28739 in contact with lignocellulosic material; and
- optionally, make the posterior collection of the generated compound.

In another embodiment, said lignocellulosic material is obtained by pre-treatment of lignocellulosic vegetal biomass, followed by hydrolysis.

The process of the invention provides the production of biofuels which comprise alcohols predominantly, especially ethanol. The process of the invention provides the production of biochemicals selected from the group which comprises, but is not limited to: succinic acid, malic acid, 1,3-propanediol, 1,2-propanediol, butanol, isobutanol, biodiesel, 1,4-butanediol, 2,3-butanediol and/or PHB—poly (butyrate hydroxide).

The present invention describes, finally, biofuels, preferably ethanol, and biochemicals produced by the process using the microorganism of the invention, such as DSM28739.

EXAMPLES

Example 1

Construction of Cassettes for the Expression and Insertion Thereof into the Genome For constructing each one of the cassettes containing genes of non-oxidative phase of the pentoses phosphate route, including gene of Xylose Isomerase, each one of genes was amplified by PCR of the S. cerevisiae genome and cloned in integrative expression cassettes.

Adjacent to the terminator of each cassette, the flanked URA3 gene was cloned by two IoxP regions in the same orientation, allowing this region to be removed by the expression of Cre recombinase and the URA3 auxotrophic marker to be used in all expression cassettes with the described genes.

With regard to the construction of the expression cassette which contains gene encoding xylose isomerase, in addition to the above-mentioned construction, in the cassette ends, 126 pb were cloned from each side with homology to a region close to the chromosome five of Saccharomyces cerevisiae, allowing the integration through homologous recombination in this region.

For the construction of expression cassette with gene encoding xylulokinase, for example, this gene was amplified by PCR of the S. cerevisiae genome and it was cloned adjacent to the promoter and terminator of the gene encoding Alcohol dehydrogenase (ADH1). After the terminator, the flanker URA3 gene was inserted by two IoxP regions in the same orientation. In the cassette ends, homology regions close to the centromere two and eight of S. cerevisiae were cloned. Two transformations were carried out to insert the cassettes expressing the gene XKS1 to 288 pb of the centromere two and the 228 pb of centromere eight. In this was, in addition to the endogenous copy, the transformant has two more copies of the gene XKS1 under the action of a high expression constitutive promoter.

In relation to the expression cassette which contains encoding genes of Transaldolase (TAL1) and Ribose 5-Phosphate Isomerase (RKI1), for example, these genes were cloned under the action of promoters and terminators of the genes Glyceraldehyde 3-Phosphate Dehydrogenase, isoenzyme 1 (TDH1) and 3-phosphoglycerate Kinase (PGK1), respectively, separated by flanked URA3 marker by the IoxP sites, and properly inserted into the host cell chromosome.

In relation to the expression cassette which contains encoding genes of Transcetolase (TKL1) and Ribose 5-Phosphate Epimerase (RPE1), for example, these genes were cloned under the action of promoters and terminators of the genes Glyceraldehyde 3-Phosphate Dehydrogenase, isoenzyme 1 (TDH1) and 3-phosphoglycerate Kinase (PGK1), respectively, separated by flanked URA3 marker by the IoxP sites, and properly inserted into the host cell chromosome.

The transformation of the host cell with each one of the cassettes containing genes of the non-oxidative phase of the pentose phosphate route followed the Gietz and Schiestl protocol [Nature Protocols 2, 31-34; 2007], through lithium acetate, and each one of the genes, flanked by strong and constitutive promoters and terminators of Saccharomyces cerevisiae, was stably integrated to the host cell chromosome. The correct integration was confirmed by PCR. After confirmation, the URA3 region was excised from genome by transient expression of Cre recombinase, leaving only one IoxP site on the place, after the terminator of inserted gene.

In the cassette ends of Xylose Isomerase, 126 pb were cloned from each side with homology to a region next to the chromosome five of Saccharomyces cerevisiae, allowing the integration through homologous recombination in this region.

Example 2

Insertion of Cassette of Xylose Isomerase into the Genome in High Number of Copies To guarantee the stable integration and high number of copies in the host cell, the cassette expressing the Xylose Isomerase represented by SEQ ID NO: 1 was modified with the inclusion, in the cassette ends, of delta elements of retrotransposon Ty1 (element present in high number of copies in to S. cerevisiae genome).

The URA3 marker flanked by the IoxP regions is replaced in this plasmid by the LEU2 marker. Previously, the LEU2 gene is deleted in a step of genetic manipulation. In this step, the URA3 gene, flanked by the IoxP regions adjacent to the homology regions to the promoter and terminator of LEU2 is integrated, resulting in the deletion of this gene. Then, the XI cassette is inserted, flanked by the Ty1elements and using the LEU2 auxotrophic marker for selecting transformants.

Example 3

Deletion of Gre3 Gene

The deletion of GRE3 gene, which encodes aldose reductase and is represented in SEQ ID NO: 14, was carried out in two steps through the genetic manipulation, aiming to reduce the production of xylitol from xylose. In the first step, the URA3 gene, flanked by the IoxP regions adjacent to the homology regions to the promoter and terminator of the GRE3 gene was integrated, resulting in the deletion of this region. In the second step, after the deletion confirmed, the URA3 marker was removed by transient expression of Cre recombinase.

Example 4

Adaptative Evolution and Consumption of Xylose

After being genetically manipulated with the insertion of all gene of the metabolic route necessary for converting xylose and before being subjected to adaptive evolution, the genetically modified microorganism, when in anaerobic conditions, consumed the xylose present in the cultivation medium slowly and with low generation of biofuel, in this case ethanol, as can be seen in FIG. 1.

Figure 2:
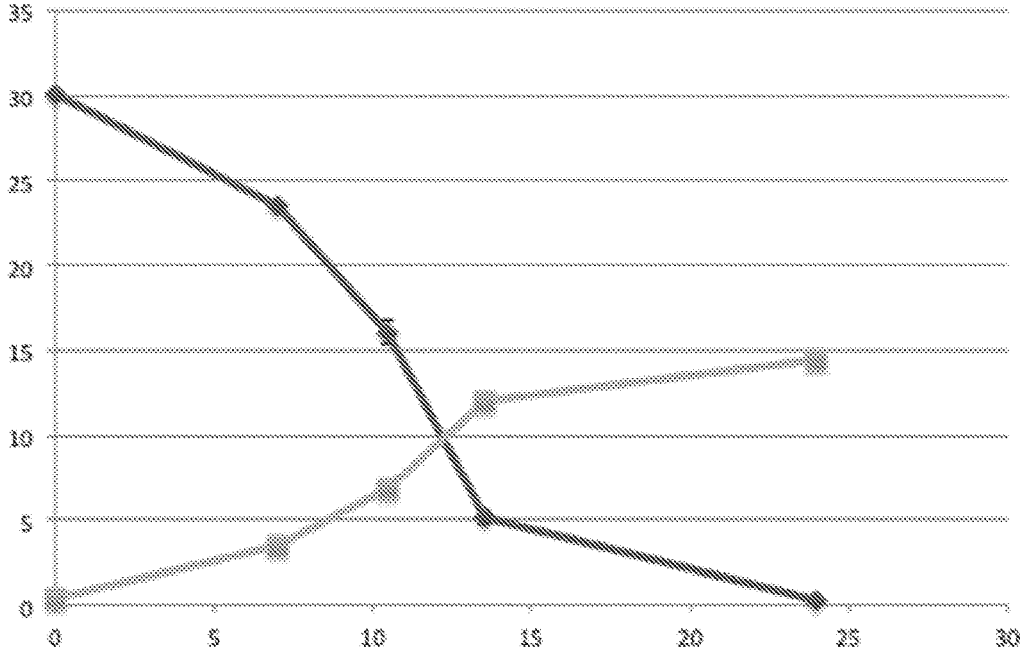
In FIG. 2, it is noted the consumption of xylose and ethanol production under anaerobic conditions by the microorganism described in the present invention after the process of genetic manipulation for insertion of genes of the pentose phosphate route and genetically modified gene of xylose isomerase, SEQ ID NO: 1, and after the evolution process. In the vertical axis, the concentration is described in g/L and in the horizontal axis, the time in hours. The concentration of xylose is indicated by (♦), while the concentration of ethanol by time is represented by (■).

Said microorganism was subjected to a process of evolutionary engineering which consisted of successive repetitions in medium containing 50 g/L of xylose under semi-anaerobic conditions. The inoculum was started with optical density (OD) of ~1.0. Due to a low initial growth, a low quantity of glucose was added to the medium in the first experiments (0.5%) aiming the culture to grow faster. After 48 hours of cultivation, an aliquot was transferred to a new flask with culture medium and the experiment was repeated. In the third transfer, it was not necessary the addition of glucose to the cultivation medium because of increased growth speed of the microorganism in xylose as the only source of carbon. 20 colonies of the mixture of evolved cells were isolated and analyzed. The microorganism DSM28739 was selected by its superior performance in terms of conversion capacity of xylose to ethanol, as can be seen in FIG. 2.

Example 5

Growth of Microorganism DSM28739 using Xylose as a Source of Carbon

Inoculum Preparation

A culture aliquot of the microorganism DSM28739 previously cryopreserved at −85° C. (in solution of glycerol 20%w/v) was reactivated in YEPD medium (20 g/L of glucose, 10 g of yeast extract and 20 g/l of peptone), during 6 hours in an Erlenmeyer of 100 mL containing 50 mL of YEPD medium, 20 g/L of glucose in an orbital shaker at 200 rpm and 30° C. Posteriorly, an aliquot of this culture was transferred to an Erlenmeyer of 500 ml containing 200 ml of YEPD medium 40 g/L of glucose.

The culture was initiated with an Optical Density (OD) equal to 0.1, when earned in 600nm of wavelength and incubated at 200 rpm and 30° C. during 16 hours. A volume of this culture was transferred to a conical bottom tube of 50 ml and centrifuged at 4000 rpm for 10 min. The pellet cells were washed 3 times in distilled water by centrifugation and resuspended in the appropriate culture medium for transference in the bioreactor (described below).

Cultivation in Bioreactor 600 mL of synthetic culture medium were prepared in a bottle of 1 L comprising xylose as one of the source of carbon, as the YEPX medium (20 g/L of xylose, 10 g/L of yeast extract and 20 g/L of bacteriological peptone). The bioreactor with work volume of 1 L was prepared with 500 mL of this culture medium.

The bioreactor was, then, sterilized in autoclave at 121° C. and 1 atm of pressure for 20 minutes. The remaining 100 mL were transferred to a bottle of 250 mL and also autoclaved. The source of carbon was dissolved in 100 mL of distilled and autoclaved water in a bottle of 250 mL. After autoclaving, the 100 mL containing the source of carbon were transferred to a bioreactor.

The inoculum was prepared from cells obtained by centrifugation of inoculum previously prepared with culture of the microorganism DSM28739. The cells were then resuspended in 100 mL of the medium without source of carbon and immediately inoculated in the bioreactor. The culture was initiated with OD=3.

During the cell growth, pH was kept in a pH range between 3 and 7, through addition of acids and/or bases. The temperature and the stirring speed were also kept constant in 30° C. and 200 rpm, respectively.

To guarantee the anaerobiosis state, before inoculation, the cultivation medium and the atmosphere of bioreactor with the nitrogen gas flow of 2 LN/min (normal liter per minute) during 10 minutes. Two samples of 1.5 mL were collected, approximately at each three hours. One sample was used to measure the OD, while the other was analyzed by high performance liquid chromatography (HPLC).

Quantification of Fermentation Products

The quantification of xylose, ethanol and glycerol was carried out by high performance liquid chromatography HPLC and using Alliance HT (Waters) chromatograph with refractive index detector (Waters 2414). The runs were performed using a column HPX-87H (BioRad) kept at 35° C., with 4 mM sulfuric acid as mobile phase and a flow of 0.6 mL/min.

Figure 3:
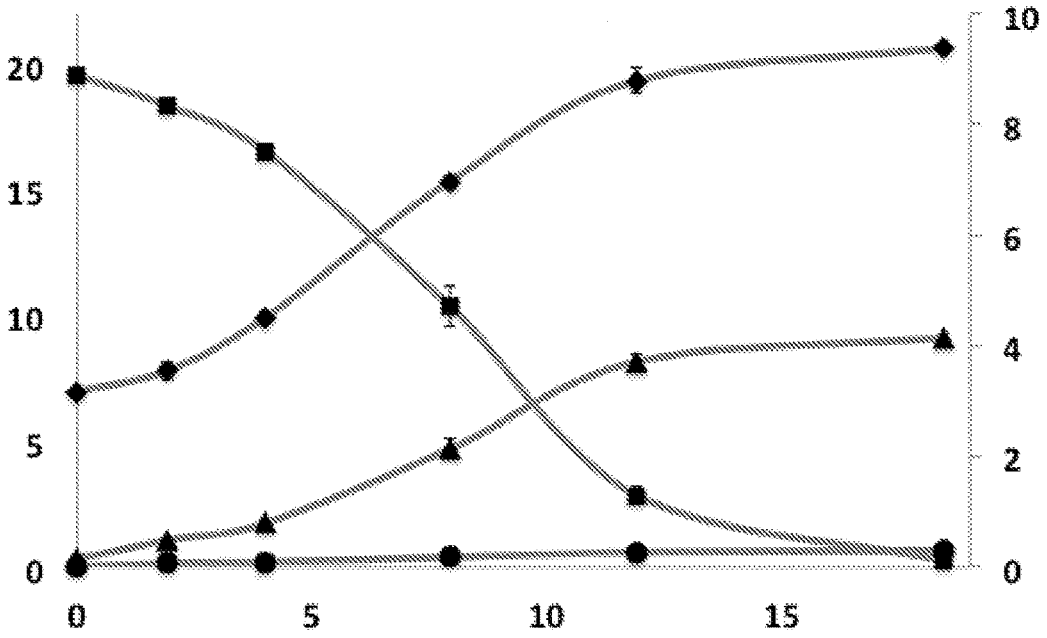
In FIG. 3, it is possible to observe the fermentation kinetics of the microorganism DSM28739 in synthetic medium comprising xylose as one of its source of carbon, as YEPX (20 g/L of xylose, 10 g/L of yeast extract and 20 g/L of bacteriological peptone). In the figure, the symbol (■) represents Xylose, (♦) represents cell growth expressed in optical density (OD), (▲) represents ethanol and (●) represents glycerol. In the presented figure, the vertical axis to the left represents the concentration (g/L) of each one of the analyzed compounds. The vertical axis to the right represents the Optical Density (OD) measured in 600 nm of absorbance. The horizontal axis, in turn, represents the fermentation time, expressed in hours.

Observing FIG. 3, it is possible to check that microorganism DSM28739 consumed 20 g/L of xylose in approximately 18 hours. The main fermentation product was the ethanol reaching approximately 9 g/L. Glycerol was also observed, but in low concentration. The glycerol production is observed in low concentration.

Table 2 shows the ethanol yield and volumetric productivity of microorganism DSM28739.

TABLE 2

Yield and volumetric productivity of microorganism DSM28739 in synthetic medium comprising xylose as one of the sources of carbon, such as the YEPX medium (20 g/L of xylose, 10 g/L of yeast extract and 20 g/L of bacteriological peptone).

| Line | Yield g/g (grams of ethanol produced by gram of consumed xylose) | Ethanol volumetric productivity of g/Lh (grams of ethanol produced per liter and per hour) |
|---|---|---|
| DSM28739 | 0.46 ± 0.01 | 0.69 ± 0.02 |

Example 6

Fermentation of Microorganism DSM28739 using Cane Straw Hydrolyzate.

Cultivation Medium

The cultivation medium was prepared using cane straw hydrolyzate containing between 20 to 60 g/L of xylose and/or 20 to 60 g/L of glucose. The hydrolyzate was supplemented with urea, in order to support the yeast growth.

Inoculum preparation

Culture aliquot of the microorganism DSM28739 previously cryopreserved at −85° C. (in solution of glycerol 20%w/v) was reactivated during 6 hours in an Erlenmeyer of 100 mL containing 50 mL of YEPD medium 20 g/L of glucose in an orbital shaker at 200 rpm and 30° C. Posteriorly, the aliquot of this culture was transferred to an Erlenmeyer of 500 ml containing 200 ml of YEPD medium 40 g/I of glucose. The culture was initiated with an OD=0.1 (optical density at 600 nm of wavelength), incubated at 200 rpm and 30° C. during 16 hours. A volume of this culture was transferred to a conical bottom tube of 50 ml and centrifuged at 4000 rpm for 10 min. The pellet cells were washed 3 times in distilled water by centrifugation and resuspended in the cultivation medium (hydrolyzed).

Cultivation in bioreactor 700 mL of cane straw hydrolizate were autoclaved in a bottle of 1 L. In the bioreactor with work volume of 1 L (previously autoclaved), 600 mL of the hydrolyzate were transferred and the remaining 100 mL were transferred to a bottle of 250 mL (previously autoclaved) for posterior resuspension of the inoculum. The inoculum was prepared from cells obtained by centrifugation in the previous item. The cells to the inoculum were resuspended in the 100 mL of the hydrolyzate and immediately inoculated in the bioreactor. The culture was initiated with an OD=1. During cell growth, pH was kept between 3 and 7 by automatic adding of aqueous solution of acids or bases, as, for example, KOH 3 mol/L or $H_2SO_4$ 1 mol/L. The temperature and the stirring speed were kept constant in 30° C. and 200 rpm respectively. To guarantee the anaerobiosis state, before inoculation, the cultivation medium and the atmosphere of the bioreactor were saturated with the nitrogen gas flow of 2 LN/min (normal liter per minute) during 10 minutes. Samples were collected in suitable intervals, immediately frozen in liquid nitrogen and kept frozen at −20° C. to posterior analysis by high performance liquid chromatography (HPLC).

Quantification of Fermentation Products

Figure 4:
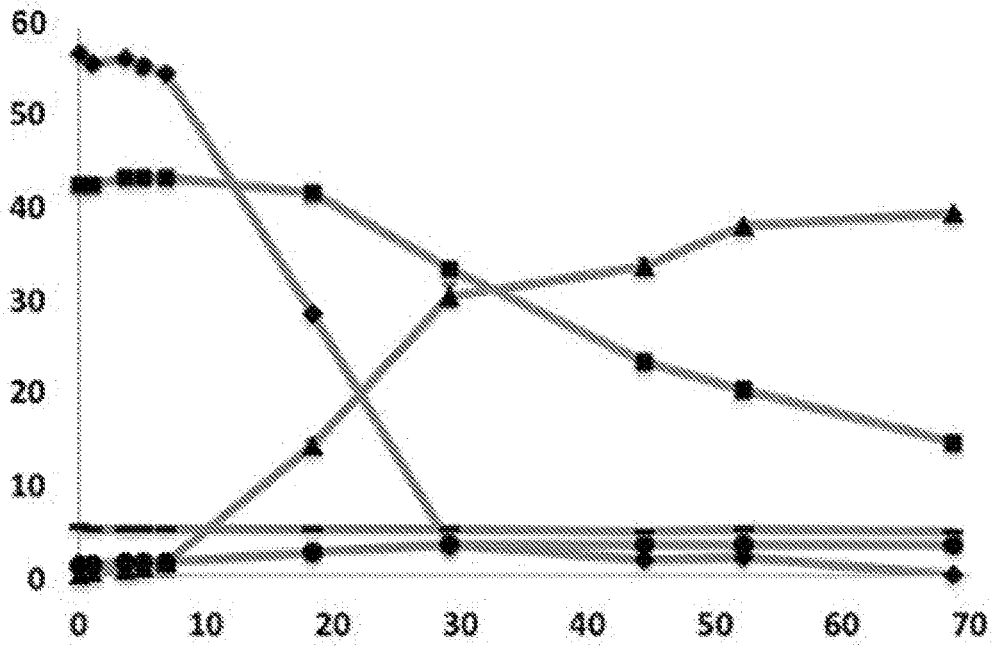
In FIG. 4, it is observed the fermentation kinetics of the microorganism DSM28739 in cane straw hydrolyzate, the concentration being represented in the vertical axis (g/L) and the time in hours in the horizontal axis. The concentration of xylose by time is represented by (■), glucose by (♦), the concentration of ethanol is represented by (▲), glycerol by (●) and acetic acid.

The quantification of xylose, ethanol and glycerol were carried out by high performance liquid chromatography HPLC and using the Alliance HT (Waters) chromatograph with refractive index detector (Waters 2414). The runs were performed using a column HPX-87H (BioRad) kept at 35° C., with 4 mM sulfuric acid as mobile phase and a flow of 0.6 mL/min. The fermentation kinetics of the microorganism DSM28739 in cane straw hydrolyzate, can be observed in FIG. 4.

The microorganism DSM28739 consumed glucose very fast in approximately 30 hours. After 70 hours, the major part of xylose was also consumed. The main fermentation product was ethanol, reaching approximately 37 g/L. The glycerol production is also observed in low concentration. The main inhibitor in the hydrolyzate, the acetic acid, was kept constant during all fermentation (around 5 g/L).

Table 3 shows the ethanol yield and the volumetric productivity of DSM28739 in cane straw hydrolyzate.

TABLE 3

Yield and volumetric productivity of microorganism DSM28739 in cane straw hydrolyzate.

| Line | Yield g/g (grams of ethanol produce per gram of consumed sugars) | Volumetric productivity of ethanol g/Lh (grams of ethanol produced per liter and per hour) |
|---|---|---|
| DSM28739 | 0.44 ± 0.009 | 0.64 ± 0.005 |

Example 7

Proof of Insertion of Cassettes into the Genetically Modified Microorganism DSM28739

The DNA of line DSM28739 was used as a model for the polymerase chain reaction using oligonucleotides yearning in an external region to the insertion of gene expression cassettes. For each reaction, it was used a pair of specific oligos for the external region of each inserted cassette.

After the experiment of polymerase chain reaction (PCR), an aliquot was applied to agarose gel 0.8%, stained with GelRed, and subjected to electrophoresis for separating the amplified fragments.

Figure 6:
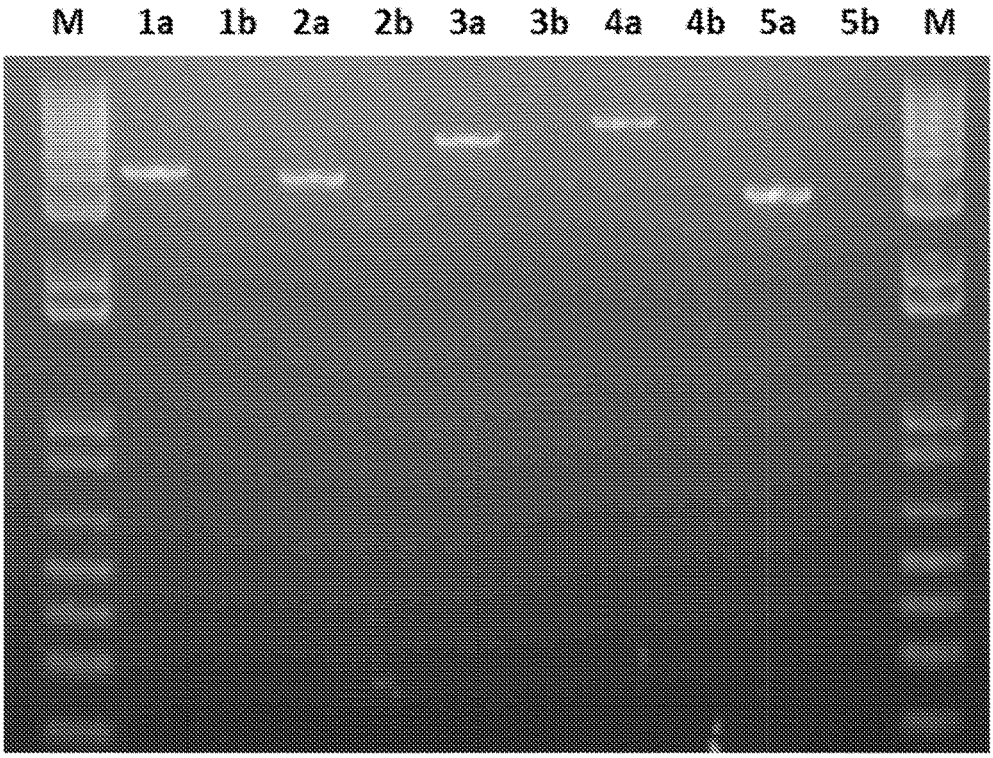
In FIG. 6, it is shown the electrophoresis gel obtained from amplification of external regions to the inserted cassette, confirming the integration to the yeasts. In the present figure, M represents the marker 1 kb ladder; 1a, the cassette of gene XKS1 inserted next to the centromere 2; 1b, the white of the reaction 1; 2a is the cassette of gene XKS1 inserted next to the centromere 8; 2b is the white of the reaction 2; 3a is the cassette of genes TAL1 and RKI1 inserted next to the centromere 12; 3b is the white of the reaction 3; 4a is the cassette of genes TKL1 and RKI1 inserted next to the centromere 13; 4b is the white of the reaction 4; 5a is the cassette of gene XI inserted next to the centromere 5; e 5b is the white of the reaction 5.
Figure 7:
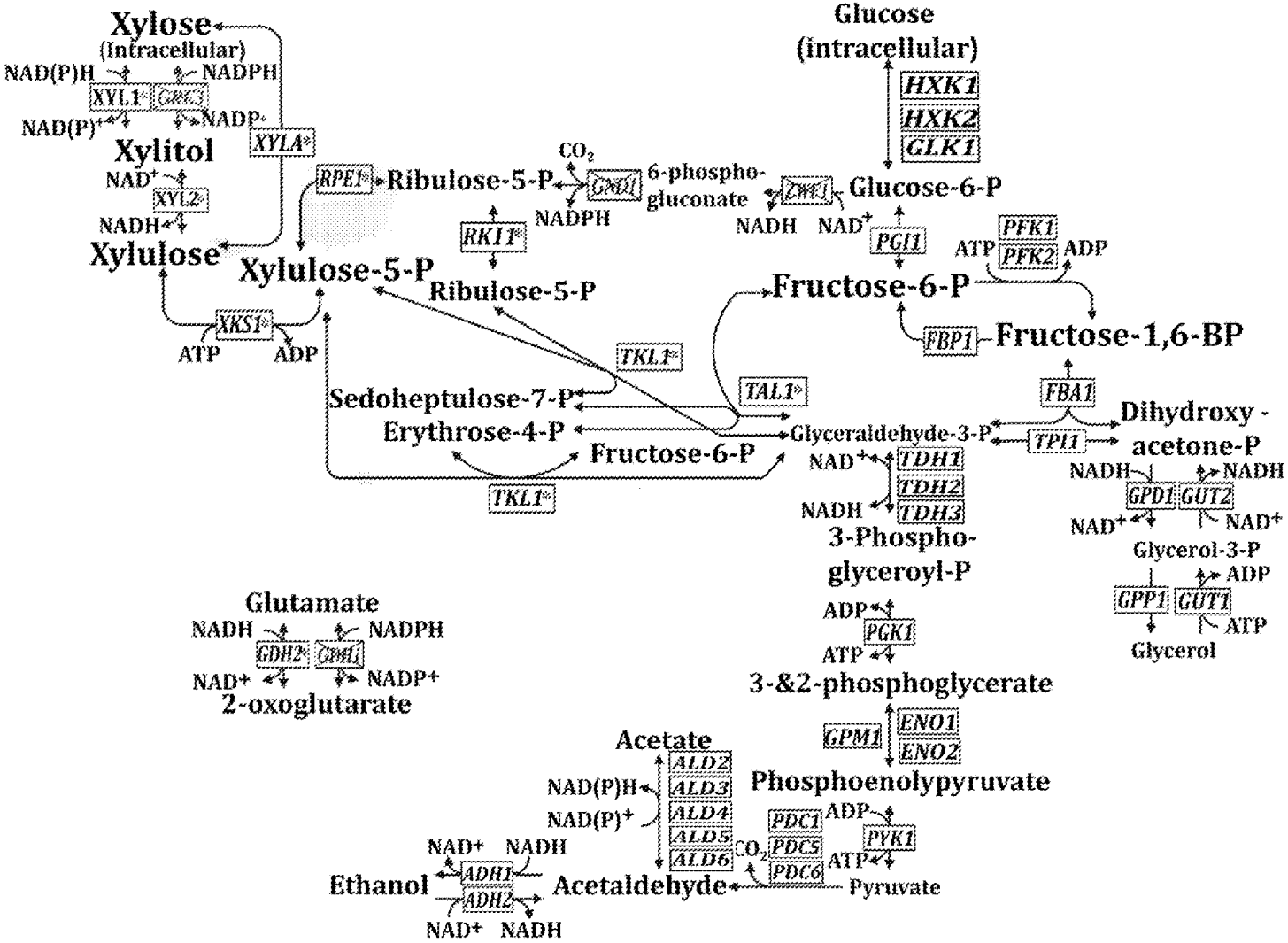
In FIG. 7, extracted from Matsushika et al., [Applied Microbiology and Biotechnology, 84:37-53, 2009], the modification made on S. cerevisiae can be viewed through the metabolic engineering for the xylose fermentation. The genes marked with asterisk were overexpressed; the crossed genes were deleted.

FIG. 6 shows the electrophoresis gel obtained from external reactions to the inserted cassettes, proving the integration to yeasts. In this figure, M represents the marker 1 kb ladder; 1a, is the cassette of gene XKS1 inserted next to the centromere 2; 1b, the white of the reaction 1; 2a is the cassette of gene XKS1 inserted next to the centromere 8; 2b is the white of the reaction 2; 3a is the cassette of genes TAL1 and RKI1 inserted next to the centromere 12; 3b is the white of the reaction 3; 4a is the cassette of genes TKL1 and RKI1 inserted next to the centromere 13; 4b is the white of the reaction 4; 5a is the cassette of gene XI inserted next to the centromere 5; and 5b is the white of the reaction 5.

Therefore, it is possible to observe in FIG. 6 that the cassettes were inserted correctly in the intended location. This result is observed due to the amplification of bands with similar size to the constructed cassette.

SEQUENCE LISTING

<160> NUMBER OF SEQ ID NOS: 17

<210> SEQ ID NO 1
<211> LENGTH: 1314
<212> TYPE: DNA
<213> ORGANISM: Artificial Sequence
<220> FEATURE:
<223> OTHER INFORMATION: Encoding sequence of peptide with feature of
xylose isomerase

<400> SEQUENCE: 1 atgactaaag aatattttcc aactattggt aaaattagat ttgaaggtaa agattctaag 60 aatccaatgg ccttccatta ctatgatgct gaaaaagaag tcatgggtaa gaaaatgaaa 120 gattggttaa gatttgccat ggcctggtgg catactttgt gcgccgatgg tgctgaccaa 180 ttcggtgttg gtactaagtc ttttccatgg aatgaaggta ctgacccaat tgctattgcc 240 aaacaaaagg ttgatgctgg ttttgaaatt atgaccaaat tgggtattga acattattgt 300 ttccacgatg ttgatttagt ttctgaaggt aattctattg aagaatatga atctaacttg 360 aaacaagttg ttgcttactt gaaacaaaag caacaagaaa ctggtattaa attattgtgg 420 tctactgcca atgtttttgg taatccaaga tatatgaacg gtgcctctac taatccagac 480 tttgatgtcg tcgccagagc tattgttcaa attaagaacg ccatggacgc cggtattgaa 540 ttgggtgctg aaaactacgt cttctggggt ggtagagaag gttatatgtc attgttaaac 600 actgaccaaa aaagagaaaa ggaacatatg gctactatgt tgactatggc tagagattac 660 gctagatcta aaggttttaa gggtactttc ttaattgaac caaaaccaat ggaaccaacc 720 aagcatcaat atgacgttga tactgaaact gttattggtt tcttgagagc tcacaattta 780 gacaaagact ttaaggtcaa cattgaagtt aatcacgcta ctttagctgg tcatactttc 840 gaacacgaat tggcctgtgc tgttgatgct ggtatgttag gttctattga tgctaacaga 900 ggtgactatc aaaatggttg ggacactgat caattcccaa ttgatcaata tgaattggtc 960 caagcttgga tggaaattat cagaggtggt ggttttgtta ctggtggtac caacttcgat 1020 gccaaaacta gaaggaactc taccgattta gaagatatta tcattgctca tatttctggt 1080 atggatgcca tggctagagc tttggaaaat gctgccaagt tattgcaaga atctccatat 1140 tgtaatatga aaaaggaaag atacgcttct tttgactctg gtattggtaa agactttgaa 1200 gatggtaagt taactttgga acaagtttac gaatatggta aaaagaatgg tgaaccaaaa 1260 gttacttctg gtaagcaaga attatatgaa gctattgttg ccatgtacca ataa 1314

<210> SEQ ID NO 2
<211> LENGTH: 742
<212> TYPE: DNA
<213> ORGANISM: Artificial Sequence
<220> FEATURE:
<223> OTHER INFORMATION: Glyceraldehyde 3-Phosphate Dehydrogenase
Promoter, isoenzyme 1 (TDH1)

<400> SEQUENCE: 2 aatgtatatg ctcatttaca ctccatatca ccatatggag gataagttgg gttgagcttc 60 tgatccaatt tattctatcc attagttgct gatatgtccc accagccaac acttgatagt 120 atctactcgc cattcacttc cagcagcgcc agtagggttg ttgagcttag taaaaatgtg 180 cgcaccacaa gcctacatgt ctccacgtca catgaaacca caccgtgggg ccttgttgcg 240 ctaggaatag gatatgcgac gaagacgctt ctgcttagta accacaccac attttcaggg 300 ggtcgatctg cttgcttcct ttactgtcac gagcggccca taatcgcgct tttttttaa 360 aagacgcgag acagcaaaca ggaagctcgg gtttcaacct tcggagtggt cgcagatctg 420 gagactggat ctttacaata cagtaaggca agccaccatc tgcttcttag gtgcatgcga 480 cggtatccac gtgcagaaca acatagtctg aagaaggggg gaggagcatg ttcattctct 540 gtagcagtaa gagcttggtg ataatgacca aaactggagt ctcgaaatca tataaataga 600 caatatattt tcacacaatg agatttgtag tacagttcta ttctctctct tgcataaata 660 agaaattcat caagaacttg gtttgatatt tcaccaacac acacaaaaaa cagtacttca 720 ctaaatttac acacaaaaca aa 742

<210> SEQ ID NO 3
<211> LENGTH: 305
<212> TYPE: DNA
<213> ORGANISM: Artificial Sequence
<220> FEATURE:
<223> OTHER INFORMATION: Glyceraldehyde 3-Phosphate Dehydrogenase
Terminator, isoenzyme 1

<400> SEQUENCE: 3 ataaagcaat cttgatgagg ataatgattt ttttttgaat atacataaat actaccgttt 60 ttctgctaga ttttgtaaag acgtaaataa gtacatatta ctttttaagc caagacaaga 120 ttaagcatta actttaccct tttctcttct aagttttaac actagttatc actgttaaaa 180 aattatggcg agaacgtcgg cggttaaaat atattaccct gaatgtggtg aattgaagtt 240 cttggatggt ttaaagattt ttccttttttg ggaaataagt aaacaatata ttgctgcctt 300 tgcaa 305

<210> SEQ ID NO 4
<211> LENGTH: 1349
<212> TYPE: DNA
<213> ORGANISM: Artificial Sequence
<220> FEATURE:
<223> OTHER INFORMATION: Encoding sequence of URA3 and loxp genes

<400> SEQUENCE: 4 cactataggg cgaattgggc ccgacgtcgc atgctcccgg ccgccatggc ggccgcggga 60 attcgatata acttcgtata gcatacatta tacgaagtta tggtccataa agcttttcaa 120 ttcatctttt tttttttgt tctttttttt gattccggtt tctttgaaat ttttttgatt 180 cggtaatctc cgagcagaag gaagaacgaa ggaaggagca cagacttaga ttggtatata 240 tacgcatatg tggtgttgaa gaaacatgaa attgcccagt attcttaacc caactgcaca 300 gaacaaaaac ctgcaggaaa cgaagataaa tcatgtcgaa agctacatat aaggaacgtg 360 ctgctactca tcctagtcct gttgctgcca agctatttaa tatcatgcac gaaaagcaaa 420 caaacttgtg tgcttcattg gatgttcgta ccaccaagga attactggag ttagttgaag 480 cattaggtcc caaaatttgt ttactaaaaa cacatgtgga tatcttgact gatttttcca 540 tggagggcac agttaagccg ctaaaggcat tatccgccaa gtacaatttt ttactcttcg 600 aagacagaaa atttgctgac attggtaata cagtcaaatt gcagtactct gcgggtgtat 660 acagaatagc agaatgggca gacattacga atgcacacgg tgtggtgggc ccaggtattg 720 ttagcggttt gaagcaggcg gcggaagaag taacaaagga acctagaggc cttttgatgt 780 tagcagaatt gtcatgcaag ggctccctag ctactggaga atatactaag ggtactgttg 840 acattgcgaa gagcgacaaa gattttgtta tcggctttat tgctcaaaga gacatgggtg 900 gaagagatga aggttacgat tggttgatta tgacacccgg tgtgggttta gatgacaagg 960

```
gagacgcatt gggtcaacag tatagaaccg tggatgatgt ggtctctaca ggatctgaca   1020

ttattattgt tggaagagga ctatttgcaa agggaaggga tgctaaggta gagggtgaac   1080

gttacagaaa agcaggctgg gaagcatatt tgagaagatg cggccagcaa aactaaaaaa   1140

ctgtattata agtaaatgca tgtatactaa actcacaaat tagagcttca atttaattat   1200

atcagttatt acccgggaat ctcggtcgta atgatttcta taacttcgta tagcatacat   1260

tatacgaagt tatatcacta gtgaattcgc ggccgcctgc aggtcgacca tatgggagag   1320

ctcccaacgc gttggatgca tagcttgag                                     1349
```

```
<210> SEQ ID NO 5
<211> LENGTH: 1008
<212> TYPE: DNA
<213> ORGANISM: Artificial Sequence
<220> FEATURE:
<223> OTHER INFORMATION: Transaldolase (TAL1)

<400> SEQUENCE: 5

atgtctgaac cagctcaaaa gaaacaaaag gttgctaaca actctctaga acaattgaaa     60

gcctccggca ctgtcgttgt tgccgacact ggtgatttcg gctctattgc caagtttcaa    120

cctcaagact ccacaactaa cccatcattg atcttggctg ctgccaagca accaacttac    180

gccaagttga tcgatgttgc cgtggaatac ggtaagaagc atggtaagac caccgaagag    240

caagtcgaaa atgctgtgga cagattgtta gtcgaattcg gtaaggagat cttaaagatt    300

gttccaggca gagtctccac cgaagttgat gctagattgt cttttgacac tcaagctacc    360

attgaaaagg ctagacatat cattaaattg tttgaacaag aaggtgtctc caaggaaaga    420

gtccttatta aaattgcttc cacttgggaa ggtattcaag ctgccaaaga attggaagaa    480

aaggacggta tccactgtaa tttgactcta ttattctcct tcgttcaagc agttgcctgt    540

gccgaggccc aagttacttt gatttcccca tttgttggta gaattctaga ctggtacaaa    600

tccagcactg gtaaagatta caagggtgaa gccgacccag gtgttatttc cgtcaagaaa    660

atctacaact actacaagaa gtacggttac aagactattg ttatgggtgc ttctttcaga    720

agcactgacg aaatcaaaaa cttggctggt gttgactatc taacaatttc tccagcttta    780

ttggacaagt tgatgaacag tactgaacct ttcccaagag ttttggaccc tgtctccgct    840

aagaaggaag ccggcgacaa gatttcttac atcagcgacg aatctaaatt cagattcgac    900

ttgaatgaag acgctatggc cactgaaaaa ttgtccgaag gtatcagaaa attctctgcc    960

gatattgtta ctctattcga cttgattgaa aagaaagtta ccgcttaa                1008
```

```
<210> SEQ ID NO 6
<211> LENGTH: 873
<212> TYPE: DNA
<213> ORGANISM: Artificial Sequence
<220> FEATURE:
<223> OTHER INFORMATION: 3-Phosphate Kinase Promoter (PGK1)

<400> SEQUENCE: 6

tactgtaatt gcttttagtt gtgtattttt agtgtgcaag tttctgtaaa tcgattaatt     60

tttttttctt tcctcttttt attaacctta atttttattt tagattcctg acttcaactc    120

aagacgcaca gatattataa catctgcata ataggcattt gcaagaatta ctcgtgagta    180

aggaaagagt gaggaactat cgcatacctg catttaaaga tgccgatttg ggcgcgaatc    240

ctttattttg gcttcaccct catactatta tcagggccag aaaaaggaag tgtttccctc    300
```

```
cttcttgaat tgatgttacc ctcataaagc acgtggcctc ttatcgagaa agaaattacc    360

gtcgctcgtg atttgtttgc aaaaagaaca aaactgaaaa aacccagaca cgctcgactt    420

cctgtcttcc tattgattgc agcttccaat ttcgtcacac aacaaggtcc tagcgacggc    480

tcacaggttt tgtaacaagc aatcgaaggt tctggaatgg cgggaaaggg tttagtacca    540

catgctatga tgcccactgt gatctccaga gcaaagttcg ttcgatcgta ctgttactct    600

ctctctttca aacagaattg tccgaatcgt gtgacaacaa cagcctgttc tcacacactc    660

ttttcttcta accaaggggg tggtttagtt tagtagaacc tcgtgaaact tacatttaca    720

tatatataaa cttgcataaa ttggtcaatg caagaaatac atatttggtc ttttctaatt    780

cttagttttt caagttctta gatgctttct ttttctcttt tttacagatc atcaaggaag    840

taattatcta ctttttacaa caaatataaa aca                                 873
```

<210> SEQ ID NO 7
<211> LENGTH: 777
<212> TYPE: DNA
<213> ORGANISM: Artificial Sequence
<220> FEATURE:
<223> OTHER INFORMATION: Ribose 5-Phosphate Isomerase (RKi1)

<400> SEQUENCE: 7

```
atggctgccg gtgtcccaaa aattgatgcg ttagaatctt tgggtaatcc tttggaggat     60

gccaagagag ctgcagcata cagagcagtt gatgaaaatt taaaatttga tgatcacaaa    120

ataattggaa ttggtagtgg tagcacagtg gtttatgttg ccgaaagaat tggacaatat    180

ttgcatgacc ctaaatttta tgaagtagcg tctaaattca tttgcattcc aacaggattc    240

caatcaagaa acttgatttt ggataacaag ttgcaattag gctccattga acagtatcct    300

cgcattgata tagcgtttga cggtgctgat gaagtggatg agaatttaca attgattaaa    360

ggtggtggtg cttgtctatt tcaagaaaaa ttggttagta ctagtgctaa aaccttcatt    420

gtcgttgctg attcaagaaa aaagtcacca aaacatttag gtaagaactg gaggcaaggt    480

gttcccattg aaattgtacc ttcctcatac gtgagggtca agaatgatct attagaacaa    540

ttgcatgctg aaaaagttga catcagacaa ggaggttctg ctaaagcagg tcctgttgta    600

actgacaata ataacttcat tatcgatgcg gatttcggtg aaatttccga tccaagaaaa    660

ttgcatagag aaatcaaact gttagtgggc gtggtggaaa caggtttatt catcgacaac    720

gcttcaaaag cctacttcgg taattctgac ggtagtgttg aagttacgga aaagtga       777
```

<210> SEQ ID NO 8
<211> LENGTH: 702
<212> TYPE: DNA
<213> ORGANISM: Artificial Sequence
<220> FEATURE:
<223> OTHER INFORMATION: Promoter of Alcohol Dehydrogenase 1 enzyme
(ADH1)

<400> SEQUENCE: 8

```
ttccgggtgt acaatatgga cttcctcttt tctggcaacc aaacccatac atcgggattc     60

ctataatacc ttcgttggtc tccctaacat gtaggtggcg gaggggagat atacaataga    120

acagatacca gacaagacat aatgggctaa acaagactac accatttaca ctgcctcatt    180

gatggtggta cataacgaac taatactgta gccctagact tgatagccat catcatatcg    240

aagtttcact accctttttc catttgccat ctattgaagt aataataggc gcatgcaact    300

tcttttcttt tttttttttt ctctctcccc cgttgttgtc tcaccatatc cgcaatgaca    360
```

```
aaaaaatgat ggaagacact aaaggaaaaa attaacgaca aagacagcac caacagatgt    420

cgttgttcca gagctgatga ggggtatctc gaagcacacg aaactttttc cttccttcat    480

tcacgcacac tactctctaa tgagcaacga tatacggcct tccttccagt tacttgaatt    540

tgaaataaaa aaagtttgct gtcttgctat caagtataaa tagacctgca attattaatc    600

ttttgtgttc tcgtcattgt tctcgttccc tttcttcctt gtttcttttt ctgcacaata    660

tttcaagcta taccaagcat acaatcaact atctcatata ca                       702


<210> SEQ ID NO 9
<211> LENGTH: 1803
<212> TYPE: DNA
<213> ORGANISM: Artificial Sequence
<220> FEATURE:
<223> OTHER INFORMATION: Xylulokinase (XKS1)

<400> SEQUENCE: 9

atgttgtgtt cagtaattca gagacagaca agagaggttt ccaacacaat gtctttagac     60

tcatactatc ttgggtttga tctttcgacc caacaactga aatgtctcgc cattaaccag    120

gacctaaaaa ttgtccattc agaaacagtg gaatttgaaa aggatcttcc gcattataac    180

acaaagaagg gtgtctatat acacggcgac actatcgaat gtcccgtagc catgtggtta    240

gaggctctag atctggttct ctcgaaatat cgcgaggcta aatttccatt gaacaaagtt    300

atggccgtct cagggtcctg ccagcagcac gggtctgtct actggtcctc ccaagccgaa    360

tctctgttag agcaattgaa taagaaaccg gaaaaagatt tattgcacta cgtgagctct    420

gtagcatttg caaggcaaac cgcccccaat tggcaagacc acagtactgc aaagcaatgt    480

caagagtttg aagagtgcat aggtgggcct gaaaaaatgg ctcaattaac agggtccaga    540

gcccatttta gatttactgg tcctcaaatt ctgaaaattg cacaattaga accagaagct    600

tacgaaaaaa caaagaccat ttctttagtg tctaattttt tgacttctat cttagtgggc    660

catcttgttg aattagagga ggcagatgcc tgtggtatga acctttatga tatacgtgaa    720

agaaaattca gtgatgagct gctacatcta attgatagtt cttctaagga taaaactatc    780

agacaaaaat taatgagagc acccatgaaa aatttgatag cgggtaccat ctgtaaatat    840

tttattgaga agtacggttt caatacaaac tgcaaggtct ctcccatgac tggggataat    900

ttagccacta tatgttcttt acccctgcgg aagaatgacg ttctcgtttc cctaggaaca    960

agtactacag ttcttctggt caccgataag tatcacccct ctccgaacta tcatcttttc   1020

attcatccaa ctctgccaaa ccattatatg ggtatgattt gttattgtaa tggttctttg   1080

gcaagggaga ggataagaga cgagttaaac aaagaacggg aaaataatta tgagaagact   1140

aacgattgga ctctttttaa tcaagctgtg ctagatgact cagaaagtag tgaaaatgaa   1200

ttaggtgtat attttcctct gggggagatc gttcctagcg taaaagccat aaacaaaagg   1260

gttatcttca atccaaaaag gggtatgatt gaaagagagg tggccaagtt caaagacaag   1320

aggcacgatg ccaaaaatat tgtagaatca caggctttaa gttgcagggt aagaatatct   1380

ccactgcttt cggattcaaa cgcaagctca caacagagac tgaacgaaga tacaatcgtg   1440

aagtttgatt acgatgaatc tccgctgcgg gactacctaa ataaaaggcc agaaaggact   1500

ttttttgtag gtggggcttc taaaaacgat gctattgtga agaagtttgc tcaagtcatt   1560

ggtgctacaa agggtaattt taggctagaa acaccaaact catgtgccct tggtggttgt   1620

tataaggcca tgtggtcatt gttatacgac tctaataaaa ttgcagttcc ttttgataaa   1680

tttctgaatg acaattttcc atggcatgta atggaaagca tatccgatgt ggataatgaa   1740
```

aattgggatc gctataattc caaaattgtc cccttaagcg aactggaaaa gactctcatc 1800 taa 1803

<210> SEQ ID NO 10
<211> LENGTH: 236
<212> TYPE: DNA
<213> ORGANISM: Artificial Sequence
<220> FEATURE:
<223> OTHER INFORMATION: Terminator of Alcohol Dehydrogenase (ADH1)

<400> SEQUENCE: 10 gcgaatttct tatgatttat gatttttatt attaaataag ttataaaaaa aataagtgta 60 tacaaatttt aaagtgactc ttaggtttta aaacgaaaat tcttattctt gagtaactct 120 ttcctgtagg tcaggttgct ttctcaggta tagcatgagg tcgctcttat tgaccacatc 180 tctaccggca tgccgagcaa atgcctgcaa atcgctcccc atttcaccca attgta 236

<210> SEQ ID NO 11
<211> LENGTH: 2043
<212> TYPE: DNA
<213> ORGANISM: Artificial Sequence
<220> FEATURE:
<223> OTHER INFORMATION: Transcetolase (TKL1)

<400> SEQUENCE: 11 atgactcaat ttactgacat tgataagcta gccgtctcca ccataagaat tttggctgtg 60 gacaccgtat ccaaggccaa ctcaggtcac ccaggtgctc cattgggtat ggcaccagct 120 gcgcacgttc tatggagtca aatgcgcatg aacccaacca acccagactg gatcaacaga 180 gatagatttg tcttgtctaa cggtcacgcg gtcgctttgt tgtattctat gctacatttg 240 actggttacg atctgtctat tgaagacttg aaacagttca gacagttggg ttccagaaca 300 ccaggtcatc ctgaatttga gttgccaggt gttgaagtta ctaccggtcc attaggtcaa 360 ggtatctcca acgctgttgg tatggccatg gctcaagcta accttgctgc cacttacaac 420 aagccaggct ttaccttgtc tgacaactac acctatgttt tcttgggtga cggttgtttg 480 caagaaggta tttcttcaga agcttcctcc ttggctggtc atttgaaatt gggtaacttg 540 attgccatct acgatgacaa caagatcact atcgatggtg ctaccagtat ctcattcgat 600 gaagatgttg ctaagagata cgaagcctac ggttgggaag ttttgtacgt agaaaatggt 660 aacgaagatc tagccggtat tgccaaggct attgctcaag ctaagttatc caaggacaaa 720 ccaactttga tcaaaatgac cacaaccatt ggttacggtt ccttgcatgc cggctctcac 780 tctgtgcacg gtgccccatt gaaagcagat gatgttaaac aactaaagag caaattcggt 840 ttcaacccag acaagtcctt tgttgttcca caagaagttt acgaccacta ccaaaagaca 900 attttaaagc caggtgtcga agccaacaac aagtggaaca agttgttcag cgaataccaa 960 aagaaattcc cagaattagg tgctgaattg gctagaagat tgagcggcca actacccgca 1020 aattgggaat ctaagttgcc aacttacacc gccaaggact ctgccgtggc cactagaaaa 1080 ttatcagaaa ctgttcttga ggatgtttac aatcaattgc cagagttgat tggtggttct 1140 gccgatttaa caccttctaa cttgaccaga tggaaggaag cccttgactt ccaacctcct 1200 tcttccggtt caggtaacta ctctggtaga tacatcagat acggtattag agaacacgct 1260 atgggtgcca tcatgaacgg tatttcagct ttcggtgcca actacaaacc atacggtggt 1320 actttcttga acttcgtttc ttatgctgct ggtgccgtta gattgtccgc tttgtctggc 1380

```
cacccagtta tttgggttgc tacacatgac tctatcggtg tcggtgaaga tggtccaaca   1440

catcaaccta ttgaaacttt agcacacttc agatccctac caaacattca agtttggaga   1500

ccagctgatg gtaacgaagt ttctgccgcc tacaagaact ctttagaatc caagcatact   1560

ccaagtatca ttgctttgtc cagacaaaac ttgccacaat tggaaggtag ctctattgaa   1620

agcgcttcta agggtggtta cgtactacaa gatgttgcta acccagatat tattttagtg   1680

gctactggtt ccgaagtatc tttgagtgtt gaagctgcta agactttggc cgcaaagaac   1740

atcaaggctc gtgttgtttc tctaccagat ttcttcactt ttgacaaaca acccctagaa   1800

tacagactat cagtcttacc agacaacgtt ccaatcatgt ctgttgaagt tttggctacc   1860

acatgttggg gcaaatacgc tcatcaatcc ttcggtattg acagatttgg tgcctccggt   1920

aaggcaccag aagtcttcaa gttcttcggt ttcaccccag aaggtgttgc tgaaagagct   1980

caaaagacca ttgcattcta taagggtgac aagctaattt ctcctttgaa aaaagctttc   2040

taa                                                                 2043
```

<210> SEQ ID NO 12
<211> LENGTH: 717
<212> TYPE: DNA
<213> ORGANISM: Artificial Sequence
<220> FEATURE:
<223> OTHER INFORMATION: Ribose 5-Phosphate Epimerase (RPE1)

<400> SEQUENCE: 12

```
atggtcaaac caattatagc tcccagtatc cttgcttctg acttcgccaa cttgggttgc     60

gaatgtcata aggtcatcaa cgccggcgca gattggttac atatcgatgt catggacggc    120

cattttgttc caaacattac tctgggccaa ccaattgtta cctccctacg tcgttctgtg    180

ccacgccctg gcgatgctag caacacagaa aagaagccca ctgcgttctt cgattgtcac    240

atgatggttg aaaatcctga aaaatgggtc gacgattttg ctaaatgtgg tgctgaccaa    300

tttacgttcc actacgaggc cacacaagac cctttgcatt tagttaagtt gattaagtct    360

aagggcatca aagctgcatg cgccatcaaa cctggtactt ctgttgacgt tttatttgaa    420

ctagctcctc atttggatat ggctcttgtt atgactgtgg aacctgggtt tggaggccaa    480

aaattcatgg aagacatgat gccaaaagtg gaaactttga gagccaagtt tccccatttg    540

aatatccaag tcgatggtgg tttgggcaag gagaccatcc cgaaagccgc caaagccggt    600

gccaacgtta ttgtcgctgg taccagtgtt ttcactgcag ctgacccgca cgatgttatc    660

tccttcatga aagaagaagt ctcgaaggaa ttgcgttcta gagatttgct agattag       717
```

<210> SEQ ID NO 13
<211> LENGTH: 189
<212> TYPE: DNA
<213> ORGANISM: Artificial Sequence
<220> FEATURE:
<223> OTHER INFORMATION: 3-Phosphate Kinase Terminator (PGK1)

<400> SEQUENCE: 13

```
attgaattga attgaaatcg atagatcaat ttttttcttt tctctttccc catcctttac     60

gctaaaataa tagtttattt tatttttga atattttta tttatatacg tatatataga    120

ctattattta tcttttaatg attattaaga tttttattaa aaaaaaattc gctcctcttt    180

taatgcctt                                                            189
```

<210> SEQ ID NO 14
<211> LENGTH: 984

<212> TYPE: DNA
<213> ORGANISM: Artificial Sequence
<220> FEATURE:
<223> OTHER INFORMATION: Aldose Reductase (GRE3)

<400> SEQUENCE: 14 atgtcttcac tggttactct taataacggt ctgaaaatgc ccctagtcgg cttagggtgc 60 tggaaaattg acaaaaaagt ctgtgcgagt caaatttatg aagctatcaa attaggctac 120 cgtctattcg atggtgcttg cgactacggc aacgaaaagg aagttggtga aggtatcagg 180 aaagccatct ccgaaggtct tgtttctaga aaggatatat ttgttgtttc aaagttatgg 240 aacaattttc accatcctga tcatgtaaaa ttagctttaa agaagacctt aagcgatatg 300 ggacttgatt atttagacct gtattatatt cacttcccaa tcgccttcaa atatgttcca 360 tttgaagaga aataccctcc aggattctat acgggcgcag atgacgagaa gaaaggtcac 420 atcaccgaag cacatgtacc aatcatagat acgtaccggg ctctggaaga atgtgttgat 480 gaaggcttga ttaagtctat tggtgtttcc aactttcagg gaagcttgat tcaagattta 540 ttacgtggtt gtagaatcaa gcccgtggct ttgcaaattg aacaccatcc ttatttgact 600 caagaacacc tagttgagtt ttgtaaatta cacgatatcc aagtagttgc ttactcctcc 660 ttcggtcctc aatcattcat tgagatggac ttacagttgg caaaaaccac gccaactctg 720 ttcgagaatg atgtaatcaa gaaggtctca caaaaccatc caggcagtac cacttcccaa 780 gtattgctta gatgggcaac tcagagaggc attgccgtca ttccaaaatc ttccaagaag 840 gaaaggttac ttggcaacct agaaatcgaa aaaaagttca ctttaacgga gcaagaattg 900 aaggatattt ctgcactaaa tgccaacatc agatttaatg atccatggac ctggttggat 960 ggtaaattcc ccacttttgc ctga 984

<210> SEQ ID NO 15
<211> LENGTH: 1032
<212> TYPE: DNA
<213> ORGANISM: Artificial Sequence
<220> FEATURE:
<223> OTHER INFORMATION: CRE Recombinase

<400> SEQUENCE: 15 ctaatcgcca tcttccagca ggcgcaccat tgcccctgtt tcactatcca gggtacggat 60 atagttcatg acaatattta cattggtcca gccaccagct tgcatgatct ccggtattga 120 aactccagcg cgggccatat ctcgcgcggc tccgacacgg gcactgtgtc cagaccaggc 180 caggtatctc tgaccagagt catccttagc gccgtaaatc aatcgatgag ttgcttcaaa 240 aatcccttcc agggcgcgag ttgatagctg gctggtggca gatggcgcgg caacaccatt 300 ttttctgacc cggcaaaaca ggtagttatt cggatcatca gctacaccag agacggaaat 360 ccatcgctcg accagtttag ttacccccag gctaagtgcc ttctctacac ctgcggtgct 420 aaccagcgtt ttcgttctgc caatatggat taacattctc ccaccgtcag tacgtgagat 480 atctttaacc ctgatcctgg caatttcggc tatacgtaac agggtgttat aagcaatccc 540 cagaaatgcc agattacgta tatcctggca gcgatcgcta ttttccatga gtgaacgaac 600 ctggtcgaaa tcagtgcgtt cgaacgctag agcctgtttt gcacgttcac cggcatcaac 660 gttttctttt cggatccgcc gcataaccag tgaaacagca ttgctgtcac ttggtcgtgg 720 cagcccggac cgacgatgaa gcatgtttag ctggcccaaa tgttgctgga tagtttttac 780 tgccagaccg cgcgcctgaa gatatagaag ataatcgcga acatcttcag gttctgcggg 840 aaaccatttc cggttattca acttgcacca tgccgcccac gaccggcaaa cggacagaag 900 cattttccag gtatgctcag aaaacgcctg gcgatccctg aacatgtcca tcaggttctt 960 gcgaacctca tcactcgttg catcgaccgg taatgcaggc aaattttggt gtacggtcag 1020 taaattggac at 1032

<210> SEQ ID NO 16
<211> LENGTH: 327
<212> TYPE: DNA
<213> ORGANISM: Artificial Sequence
<220> FEATURE:
<223> OTHER INFORMATION: L TR of retrotransposon Ty1

<400> SEQUENCE: 16 ctgagagatt ggtgaatttt gagatgattg taggcattcc attgttgatc aaggctacaa 60 tattatgtat acagaatata ctaaaagttc tcctcgaggg tagaggaatc ctcaaagggg 120 aagcgatatt tctacataat attattacga ttattcctca ttccgtttta tatgtttcat 180 tatcctatta cattatcaat ccttgcactt cagcttcctc taacttcgat gacagtttct 240 catacccttat gtcatcgtct aacaccgtat atgataatat actggtagtg tgactactag 300 tttatagacg atagttgatt tttattc 327

<210> SEQ ID NO 17
<211> LENGTH: 2216
<212> TYPE: DNA
<213> ORGANISM: Artificial Sequence
<220> FEATURE:
<223> OTHER INFORMATION: LEU2 (ORF + promoter and terminator)

<400> SEQUENCE: 17 tcgaggagaa cttctagtat atccacatac ctaatattat tgccttatta aaaatggaat 60 cccaacaatt acatcaaaat ccacattctc ttcaaaatca attgtcctgt acttccttgt 120 tcatgtgtgt tcaaaaacgt tatatttata ggataattat actctatttc tcaacaagta 180 attggttgtt tggccgagcg gtctaaggcg cctgattcaa gaaatatctt gaccgcagtt 240 aactgtggga atactcaggt atcgtaagat gcaagagttc gaatctctta gcaaccatta 300 tttttttcct caacataacg agaacacaca ggggcgctat cgcacagaat caaattcgat 360 gactggaaat tttttgttaa tttcagaggt cgcctgacgc atataccttt ttcaactgaa 420 aaattgggag aaaaaggaaa ggtgagaggc cggaaccggc ttttcatata gaatagagaa 480 gcgttcatga ctaaatgctt gcatcacaat acttgaagtt gacaatatta tttaaggacc 540 tattgttttt tccaataggt ggttagcaat cgtcttactt tctaactttt cttacctttt 600 acatttcagc aatatatata tatatttcaa ggatatacca ttctaatgtc tgcccctaag 660 aagatcgtcg ttttgccagg tgaccacgtt ggtcaagaaa tcacagccga agccattaag 720 gttcttaaag ctatttctga tgttcgttcc aatgtcaagt tcgatttcga aaatcattta 780 attggtggtg ctgctatcga tgctacaggt gtcccacttc cagatgaggc gctggaagcc 840 tccaagaagg ttgatgccgt tttgttaggt gctgtgggtg gtcctaaatg gggtaccggt 900 agtgttagac ctgaacaagg tttactaaaa atccgtaaag aacttcaatt gtacgccaac 960 ttaagaccat gtaactttgc atccgactct cttttagact tatctccaat caagccacaa 1020 tttgctaaag gtactgactt cgttgttgtc agagaattag tgggaggtat ttactttggt 1080 aagagaaagg aagacgatgg tgatggtgtc gcttgggata gtgaacaata caccgttcca 1140 gaagtgcaaa gaatcacaag aatggccgct ttcatggccc tacaacatga gccaccattg 1200

-continued

```
cctatttggt ccttggataa agctaatgtt ttggcctctt caagattatg gagaaaaact   1260
gtggaggaaa ccatcaagaa cgaattccct acattgaagg ttcaacatca attgattgat   1320
tctgccgcca tgatcctagt taagaaccca acccacctaa atggtattat aatcaccagc   1380
aacatgtttg gtgatatcat ctccgatgaa gcctccgtta tcccaggttc cttgggtttg   1440
ttgccatctg cgtccttggc ctctttgcca gacaagaaca ccgcatttgg tttgtacgaa   1500
ccatgccacg gttctgctcc agatttgcca aagaataagg ttgaccctat cgccactatc   1560
ttgtctgctg caatgatgtt gaaattgtca ttgaacttgc ctgaagaagg taaggccatt   1620
gaagatgcag ttaaaaaggt tttggatgca ggtatcagaa ctggtgattt aggtggttcc   1680
aacagtacca ccgaagtcgg tgatgctgtc gccgaagaag ttaagaaaat ccttgcttaa   1740
aaagattctc tttttttatg atatttgtac ataaacttta taaatgaaat tcataataga   1800
aacgacacga aattacaaaa tggaatatgt tcatagggta gacgaaacta tatacgcaat   1860
ctacatacat ttatcaagaa ggagaaaaag gaggatagta aaggaataca ggtaagcaaa   1920
ttgatactaa tggctcaacg tgataaggaa aaagaattgc actttaacat taatattgac   1980
aaggaggagg gcaccacaca aaaagttagg tgtaacagaa aatcatgaaa ctacgattcc   2040
taatttgata ttggaggatt ttctctaaaa aaaaaaaaat acaacaaata aaaaacactc   2100
aatgacctga ccatttgatg gagtttaagt caataccttc ttgaaccatt tcccataatg   2160
gtgaaagttc cctcaagaat tttactctgt cagaaacggc cttacgacgt agtcga       2216
```

The invention claimed is:

[1. A genetically modified microorganism, wherein the genetically modified organism is Saccharomyces cerevisiae DSM28739.]

*2. A method of genetically modifying a yeast belonging to a yeast genus, said method comprising introducing a sequence of nucleotides encoding a peptide with xylose isomerase function, into said yeast; using homologous recombination, selectively replacing codons present in said yeast with codons present in Orpinomyces, to achieve a Codon Adaptation Index of at least 0.79; using evolutionary engineering in order to generate random mutations which favor xylose conversion to biochemicals and/or biofuels; and recovering a genetically modified yeast.*

*3. The method of claim 2, wherein said Codon Adaptation Index is from 0.79 to 0.91.*

*4. The method of claim 2, said method further comprising a step of fermenting a sugar, utilizing said genetically modified yeast, to generate a fermentation product.*

*5. The method of claim 4, wherein said sugar is xylose.*

*6. The method of claim 4, wherein said fermentation product is ethanol.*

*7. The method of claim 4, wherein said sugar is xylose, wherein said fermentation product is ethanol, and wherein yield of said ethanol is at least 0.45 grams ethanol per gram xylose consumed by said genetically modified yeast in synthetic medium comprising said xylose.*

*8. The method of claim 4, wherein said sugar is xylose, wherein said fermentation product is ethanol, and wherein volumetric productivity of said ethanol is at least 0.67 grams of ethanol produced per liter per hour in synthetic medium comprising said xylose.*

*9. The method of claim 2, wherein said yeast genus is selected from the group consisting of Saccharomyces, Schefferomyces, Spathaspora, Pichia, Candida, Kluyveromyces, Schizosaccharomyces, Brettanomyces, Hansenula, and Yarrowia.*

*10. The method of claim 9, wherein said yeast genus is Saccharomyces.*

*11. The method of claim 10, wherein said genetically modified yeast is Saccharomyces cerevisiae DSM28739.*

* * * * *